United States Patent
Cuthbertson et al.

(10) Patent No.: US 8,197,793 B2
(45) Date of Patent: *Jun. 12, 2012

(54) METHODS OF RADIOFLUORINATION OF BIOLOGICALLY ACTIVE VECTORS

(75) Inventors: Alan Cuthbertson, Oslo (NO); Magne Solbakken, Oslo (NO); Joseph Maduabuchi Arukwe, Oslo (NO); Hege Karlsen, Oslo (NO); Matthias Eberhard Glaser, London (GB)

(73) Assignee: GE Healthcare AS, Oslo (NO)

( * ) Notice: Subject to any disclaimer, the term of this patent is extended or adjusted under 35 U.S.C. 154(b) by 1744 days.

This patent is subject to a terminal disclaimer.

(21) Appl. No.: 10/549,082

(22) PCT Filed: Mar. 12, 2004

(86) PCT No.: PCT/GB2004/001052
§ 371 (c)(1),
(2), (4) Date: Jul. 3, 2006

(87) PCT Pub. No.: WO2004/080492
PCT Pub. Date: Sep. 23, 2004

(65) Prior Publication Data
US 2010/0068139 A1    Mar. 18, 2010

(30) Foreign Application Priority Data

Mar. 13, 2003  (GB) .................................. 0305704.9

(51) Int. Cl.
*A61K 51/00*  (2006.01)
(52) U.S. Cl. ...................................... 424/1.69; 424/1.89
(58) Field of Classification Search ................ 424/1.11, 424/1.69, 1.89; 530/300, 317, 329
See application file for complete search history.

(56) References Cited

U.S. PATENT DOCUMENTS
7,368,474 B2 * 5/2008 Cuthbertson et al. ......... 514/453

FOREIGN PATENT DOCUMENTS
WO          99/11590         3/1999

OTHER PUBLICATIONS

Hwang, D.R., et.al., Positron-Labeled Angiotensin-Converting Enzyme (ACE) Inhibitor: Fluorine-18-Fluorocaptopril. Probing the ACE Activity in Vivo by Positron Emission Tomography Journal of Nuclear Medicine, Society of Nuclear Medicine. New York, US, vol. 32, No. 9, Sep. 1991 pp. 1730-1737.
Int'l Search Report and written opinion dated Jun. 2004 for PCT/GB2004/001052.

* cited by examiner

*Primary Examiner* — Michael G Hartley
*Assistant Examiner* — Jagadishwar Samala
(74) *Attorney, Agent, or Firm* — Yonggang Ji

(57) ABSTRACT

The invention relates to conjugates of formula (V) or (VI): wherein X is —CO—NH—, —NH—, —O—, —NH-CONH—, or —NHCSNH—; their use as radiopharmaceuticals, processes for their preparation, and synthetic intermediates used in such processes.

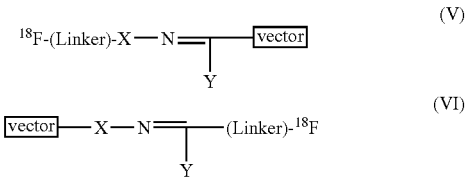

26 Claims, No Drawings

METHODS OF RADIOFLUORINATION OF BIOLOGICALLY ACTIVE VECTORS

This application is a filing under 35 U.S.C. 371 of international application number PCT/GB2004/001052, filed Mar. 12, 2004, which claims priority to application number 0305704.9 filed Mar. 13, 2003, in Great Britain the entire disclosure of which is hereby incorporated by reference.

FIELD OF INVENTION

The present invention relates to diagnostic and radiodiagnostic agents, including biologically active vectors labelled with positron-emitting nuclides. It further relates to methods and reagents for [$^{18}$F]-fluorination of vectors, where a vector is defined as a molecule with an affinity for a specific biological target, and is preferably a peptide. The resultant $^{18}$F-labelled conjugates are useful as radiopharmaceuticals, specifically for use in Positron Emission Tomography (PET).

BACKGROUND OF THE INVENTION

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

One difficulty with $^{18}$F-labelled peptides is that the existing $^{18}$F-labelling agents are time-consuming to prepare. Efficient labelling of peptides and proteins with $^{18}$F is only achieved by using suitable prosthetic groups. Several such prosthetic groups have been proposed in the literature, including N-succinimidyl-4-[$^{18}$F]fluorobenzoate, m-maleimido-N-(p-[$^{18}$F]fluorobenzyl)-benzamide, N-(p-[$^{18}$F] fluorophenyl)maleimide, and 4-[$^{18}$F]fluorophenacylbromide. Almost all of the methodologies currently used today for the labelling of peptides and proteins with $^{18}$F utilize active esters of the fluorine labelled synthon. As peptides and proteins may contain a multitude of functional groups capable of reaction with active esters these current methods are not site-specific. For example a peptide containing three lysine residues has three amine functions all equally reactive towards the labelled synthon. Therefore, there still exists a need for $^{18}$F-labelled prosthetic groups and methodologies, which allow rapid, chemoselective introduction of $^{18}$F, particularly into peptides, under mild conditions to give $^{18}$F-labelled products in high radiochemical yield and purity. Additionally, there is a need for such methodologies which are amenable to automation to facilitate preparation of radiopharmaceuticals in the clinical setting.

DETAILED DESCRIPTION OF THE INVENTION

The present invention provides a method for radiofluorination comprising reaction of a compound of formula (I) with a compound of formula (II):

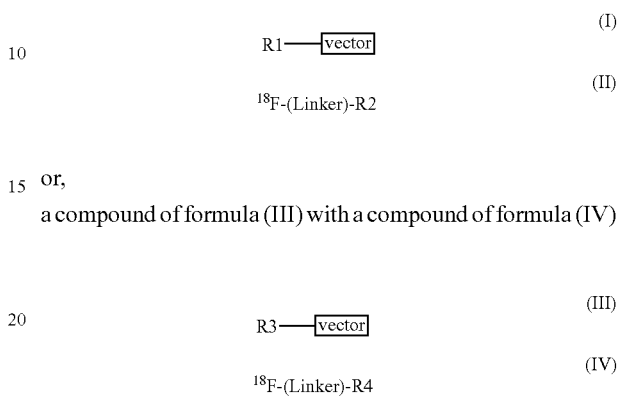

or, a compound of formula (III) with a compound of formula (IV)

wherein

R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

R2 is a functional group which, under mild conditions such as aqueous buffer, reacts site-specifically with R1 yielding a stable conjugate. R2 can be ammonia derivatives such as primary amine, secondary amine, hydroxylamine, hydrazine, hydrazide, aminoxy, phenylhydrazine, semicarbazide, or thiosemicarbazide, and is preferably a hydrazine, hydrazide or aminoxy group;

R3 is a functional group which reacts site-specifically with R4. R3 can be ammonia derivatives such as primary amine, secondary amine, hydroxylamine, hydrazine, hydrazide, aminoxy, phenylhydrazine, semicarbazide, or thiosemicarbazide, and is preferably a hydrazine, hydrazide or aminoxy group;

R4 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

to give a conjugate of formula (V) or (VI) respectively:

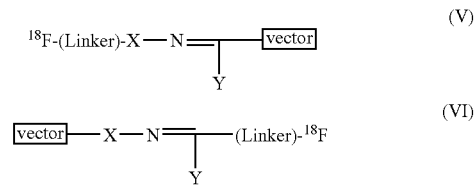

wherein X is —CO—NH—, —NH—, —O—, —NHCONH—, or —NHCSNH—, and is preferably —CO—NH—, —NH— or —O—; Y is H, alkyl or aryl substituents; and the Linker group in the compounds of formulae (II), (IV), (V) and (VI) is selected from

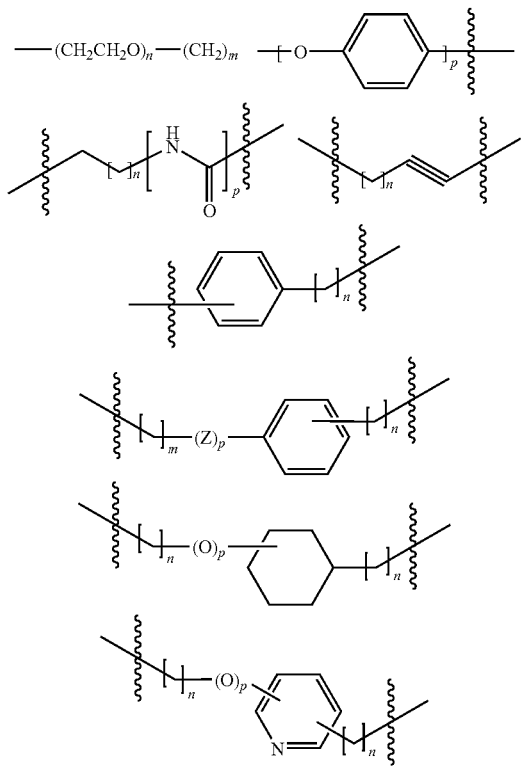

wherein:
n is an integer of 0 to 20;
m is an integer of 1 to 10;
p is an integer of 0 or 1;
Z is O or S.

The Linker group in the compounds of formulae (II), (IV), (V) and (VI) are chosen to provide good in vivo pharmacokinetics, such as favourable excretion characteristics in the resultant conjugate of formula (V) or (VI). The use of linker groups with different lipophilicities and or charge can significantly change the in vivo pharmacokinetics of the peptide to suit the diagnostic need. For example, where it is desirable for a conjugate of formula (V) or (VI) to be cleared from the body by renal excretion, a hydrophilic linker is used, and where it is desirable for clearance to be by hepatobiliary excretion a hydrophobic linker is used. Linkers including a polyethylene glycol moiety have been found to slow blood clearance which is desirable in some circumstances.

Suitably, the R1 aldehyde is generated by in situ oxidation of a precursor functionalised vector containing a 1,2-diol or 1,2 aminoalcohol group. For example, the latter can be inserted into the peptide sequence directly during synthesis using the amino acid Fmoc-Dpr(Boc-Ser)-OH described by Wahl et at in Tetrahedron Letts. 37, 6861 (1996). Similarly, an R4 aldehyde in a compound of formula (IV) may be generated by oxidation of a precursor.

Suitable oxidising agents which may be used to generate the R1 or R4 moiety in the compounds of formulae (I) and (IV) respectively, include periodate, periodic acid, paraperiodic acid, sodium metaperiodate, and potassium metaperiodate R1 and R4 in the compounds of formulae (I) and (IV) and related aspects of the invention are each preferably selected from —CHO, >C=O, —CH(—O—$C_{1-4}$alkyl-O—) such as —CH(—OCH$_2$CH$_2$O—), and —CH(OC$_{1-4}$alkyl)$_2$ such as —CH(OCH$_3$)$_2$, and in a preferred aspect R1 and R4 are —CHO.

R2 and R3 in the compounds of formulae (II) and (III) and related aspects of the invention are each preferably selected from —NHNH$_2$, —C(O)NHNH$_2$, and —ONH$_2$ and are preferably —ONH$_2$.

Y in the compounds of formulae (V) and (VI) and related aspects of the invention is preferably H, $C_{1-6}$alkyl (such as methyl), or phenyl.

The reaction may be effected in a suitable solvent, for example, in an aqueous buffer in the pH range 2 to 11, suitably 3 to 11, more suitably 3 to 6, and at a non-extreme temperature of from 5 to 70° C., preferably at ambient temperature.

The present invention provides a more chemoselective approach to radiolabelling where the exact site of introduction of the label is pre-selected during the synthesis of the peptide or vector precursor. The ligation reaction occurring at a pre-determined site in the vector gives only one possible product. This methodology is therefore chemoselective, and its application is considered generic for a wide range of peptides, biomolecules and low-molecular weight drugs.

In a further aspect, the present invention provides a method for radiofluorination comprising reaction of a compound of formula (Ia) with a compound of formula (IIa):

(Ia)
(IIa)

or,
a compound of formula (IIIa) with a compound of formula (IVa)

(IIIa)
(IVa)

wherein R1 and R4 are as defined above for the compounds of formula (I) and (IV) respectively;
the Linker group in the compounds of formulae (IIa) and (IVa) are each a $C_{1-60}$ hydrocarbyl group, suitably a $C_{1-30}$ hydrocarbyl group, optionally including 1 to 30 heteroatoms, suitably 1 to 10 heteroatoms such as oxygen or nitrogen. Suitable Linker groups include alkyl, alkenyl, alkynyl chains, aromatic, polyaromatic, and heteroaromatic rings, and polymers comprising ethyleneglycol, amino acid, or carbohydrate subunits;
to give a conjugate of formula (Va) or (VIa) respectively:

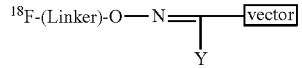
(Va)
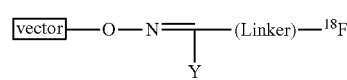
(VIa)

wherein Y is H, alkyl or aryl substituents; and the Linker group is as defined for the compound of formula (IIa) or (IVa).

The term "hydrocarbyl group" means an organic substituent consisting of carbon and hydrogen, such groups may include saturated, unsaturated, or aromatic portions.

In a preferred aspect, the present invention provides a method for radiofluorination comprising reaction of a compound of formula (VII):

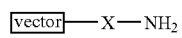
(VII)

with a compound of formula (VIII), (IX), (X) or (XI):

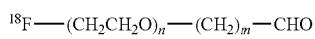
(VIII)

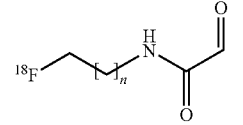
(IX)

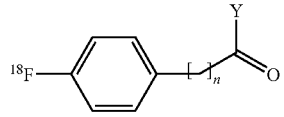
(X)

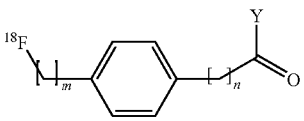
(XI)

wherein:
n is an integer of 0 to 20;
m is an integer of 1 to 10;
X is —CO—NH—, —NH— or —O— and is preferably —O—
Y is H, alkyl or aryl substituents
to give a compounds of formula (XII-XV) respectively:

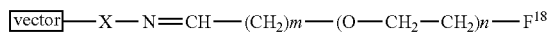
(XII)

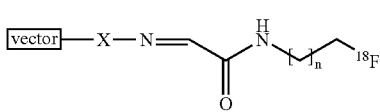
(XIII)

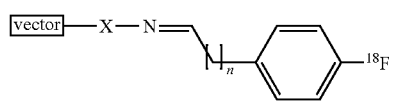
(XIV)

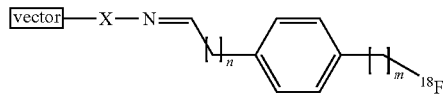
(XV)

wherein X is as defined for the compound of formula (VII), m and n are defined as for the compounds of formula (VIII to XI).

This reaction may be effected in a suitable solvent, for example, in an aqueous buffer in the pH range 2 to 11, suitably 3 to 11, more suitably 3 to 6, and at a non-extreme temperature of from 5 to 70° C., preferably at ambient temperature.

It is also considered useful when using an amine moiety in either the vector compound of formula (I) or (III) or the synthon of formula (II) or (IV) as functional group, and also in the more specifically described aspects of the invention, to include a reductive step in order to stabilise the resulting Schiff base. Suitable reducing agents for this step are well known to those skilled in the art and include sodium borohydride and sodium cyanoborohydride.

In a further preferred aspect, the present invention provides a method for radiofluorination comprising reaction of a compound of formula (XVI):

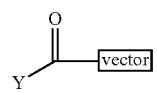
(XVI)

where Y is H, alkyl or an aryl substituent
preferably with compounds of the formula (XVII), (XVIII), (XIX) or(XX):

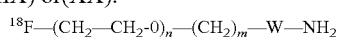
(XVII)

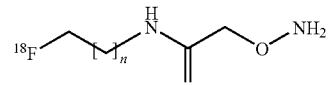
(XVIII)

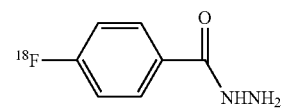
(XIX)

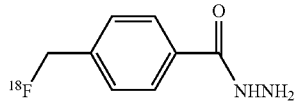
(XX)

wherein m and n are as defined for the previous compounds and W=—CONH—, —NH—or —O— to give a compound of formula (XXI), (XXII), (XXIII) or (XXIV) respectively:

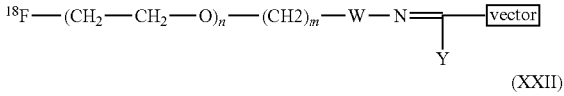
(XXI)

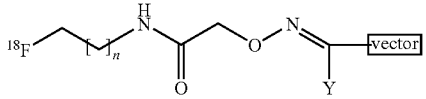
(XXII)

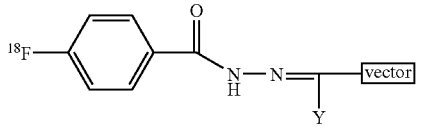
(XXIII)

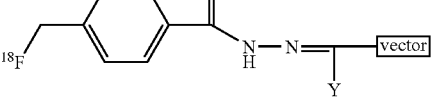
(XXIV)

wherein W=—CONH—, —NH— or —O—,
m, n, are as defined for the compounds of formula (XIII to XI) and Y is H, alkyl or aryl moiety.

This reaction may be effected in a suitable solvent, for example, in an aqueous buffer in the pH range 2 to 11, suitably 3 to 11, more suitably 3 to 6, and at a non-extreme temperature of from 5 to 70° C., preferably at ambient temperature.

In formulae (I) and (III) and in other aspects of the invention unless specifically stated otherwise, suitable vectors for labelling are peptides, which may include somatostatin analogues, such as octreotide, bombesin, vasoactive intestinal peptide, chemotactic peptide analogues, α-melanocyte stimulating hormone, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine. Preferred peptides for labelling are Arg-Gly-Asp peptide and its analogues, such as those described in WO 01/77415 and WO 03/006491. Preferred peptides comprise the fragment As will be appreciated by the skilled person, the methods of the invention may also be used for radiofluorination of other biomolecules such as proteins, hormones, oligonucleotides, and antibody fragments, as well as small drug-like molecules to provide a variety of PET tracers.

In formulae (IIa) and (IVa) and in other aspects of the invention unless specifically stated otherwise, the Linker is a $C_{1-60}$ hydrocarbyl group, suitably a $C_{1-30}$ hydrocarbyl group optionally including 1 to 30 heteroatoms, suitably 1 to 10 heteroatoms such as oxygen or nitrogen, and is chosen to provide good in vivo pharmacokinetics. Suitable Linker groups include alkyl, alkenyl, alkynyl chains, aromatic, polyaromatic, and heteroaromatic rings, and polymers comprising ethyleneglycol, amino acid, or carbohydrate subunits. Preferred Linker groups in formulae (IIa) and (IVa) and in other aspects of the invention include those selected from:

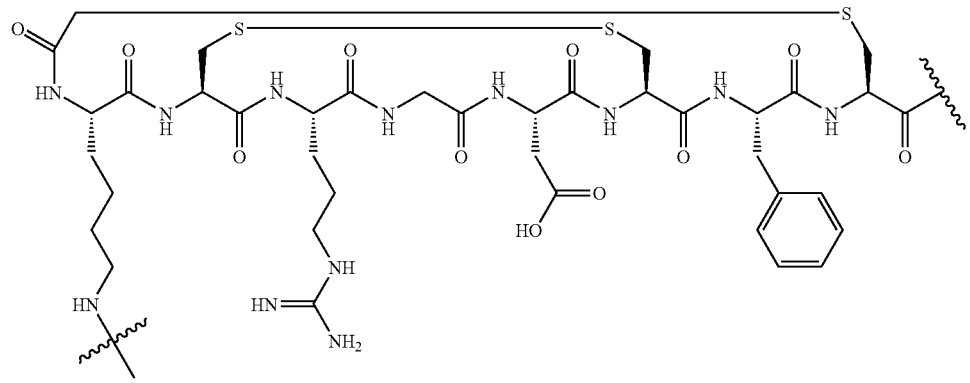

In one particular aspect, the peptide in formula (I) or (III) is of formula (A):

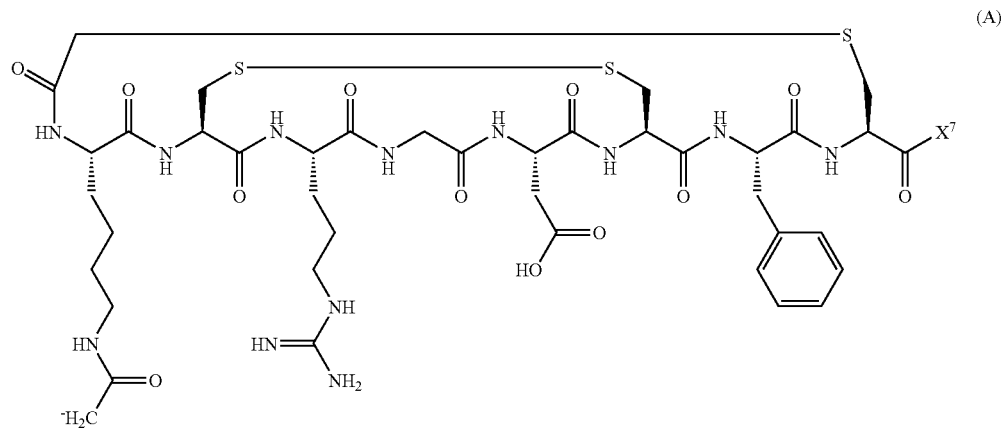

wherein $X^7$ is either —$NH_2$ or

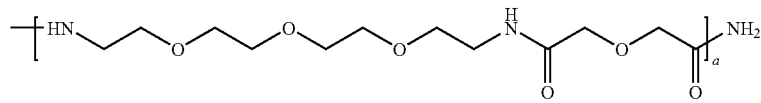

wherein a is an integer of from 1 to 10, preferably a is 1.

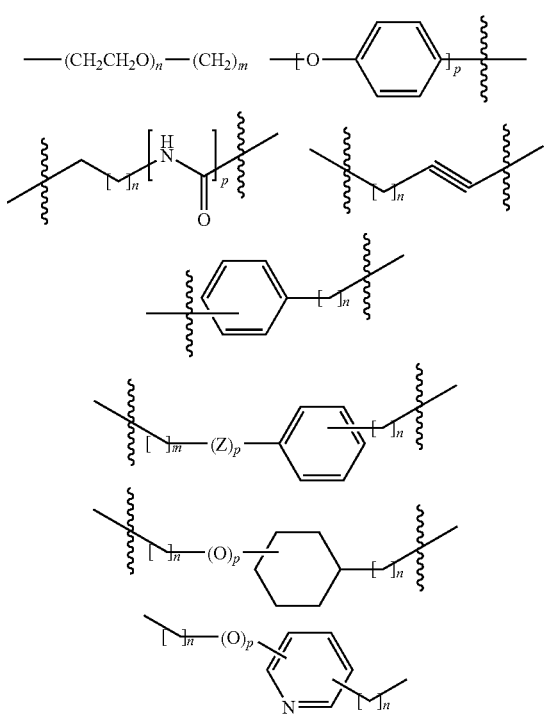

wherein:
n is an integer of 0 to 20;
m is an integer of 1 to 10;
p is an integer of 0 or 1;
Z is O or S.

Particularly preferred linker groups in formulae (IIa) and (IVa) and in other aspects of the invention may be selected from:

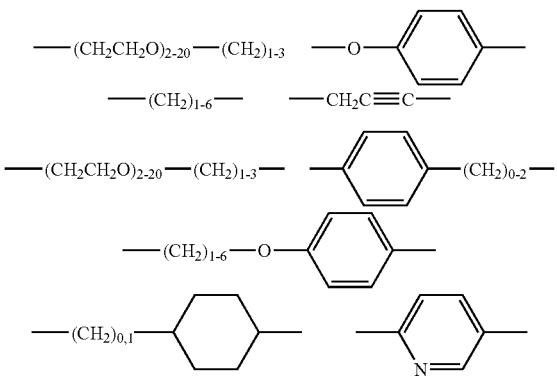

Compounds of formula (I) and (III) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the group R1 and R3 in a compound of formula (I) or (III) may be achieved by reaction of the N or C-terminus of the peptide or with some other functional group contained within the peptide sequence, modification of which does not affect the binding characteristics of the vector. In a preferred example the aminoxy group, $NH_2$—O— may be directly introduced into the peptide sequence using the amino acids Fmoc-Ams(Boc)-OH or Fmoc-Dpr(Boc-Aoa)-OH supplied by Novabiochem. The functional groups R1 and R3 are preferably introduced by formation of a stable amide bond formed by reaction of a peptide amine function with an activated acid and introduced either during or following the peptide synthesis. When the precursor is an acid then R1 and R3 can be introduced using in situ activating agents such as 2-(1H-benzotriazole-1-yl)-1,1,3,3-tetramethyluronium hexafluorophosphate (HBTU) or N-[(dimethylamino)-1H-1,2,3-triazolo[4,5-b]pyridin-1-ylmethylene]-N-methylmethanaminium hexafluorophosphate N-oxide (HATU).

In another aspect, the present invention provides novel $^{18}F$-prosthetic groups, useful for labelling peptides and proteins, for example by the methods described above.

Accordingly, there is provided a compound of formula (II) or formula (IV), or a compound of formula (IIa), (IVa), (VIII), (IX), (X), (XI), (XVII), (XVIII), (XIX), or (XX); all as defined above with the provisos:

(i) in the compounds of formula (II), if the linker is phenyl then R2 is aminoxy (suitably —$ONH_2$);

(ii) in the compounds of formula (IV), the linker is not phenyl;

(iii) in the compounds of formula (IVa), the linker is not phenyl or phenyl substituted by halo, hydroxy, or benzyloxy;

(iv) in the compounds of formula (X), n is not 0.

Preferred compounds of formula (IV) for use in the processes described herein, and which are claimed per se include:

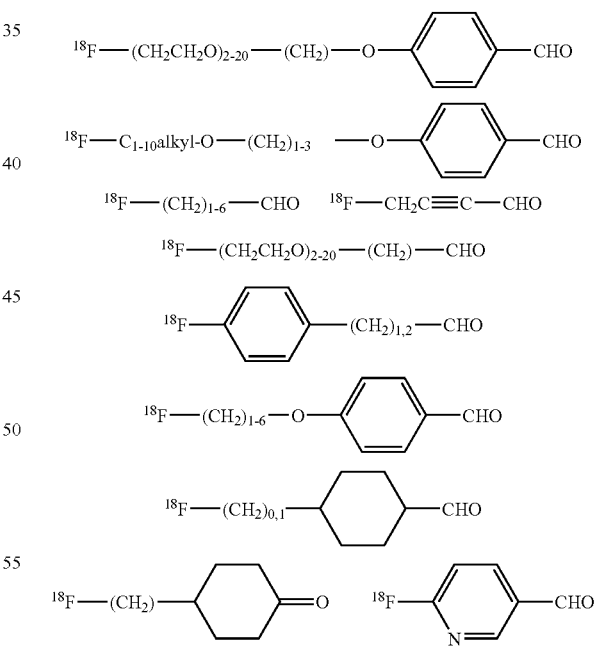

In another aspect, the present invention provides compounds of formula (I) and (III) as well as the compounds of formula (Ia), (IIIa), (VII), (XVI); all as defined above. Preferred compounds of formula (I), (III), (Ia), (IIIa), (VII), and (XVI) are those wherein the vector is Arg-Gly-Asp peptide or an analogue thereof as described above, and especially where the vector is of formula (A):

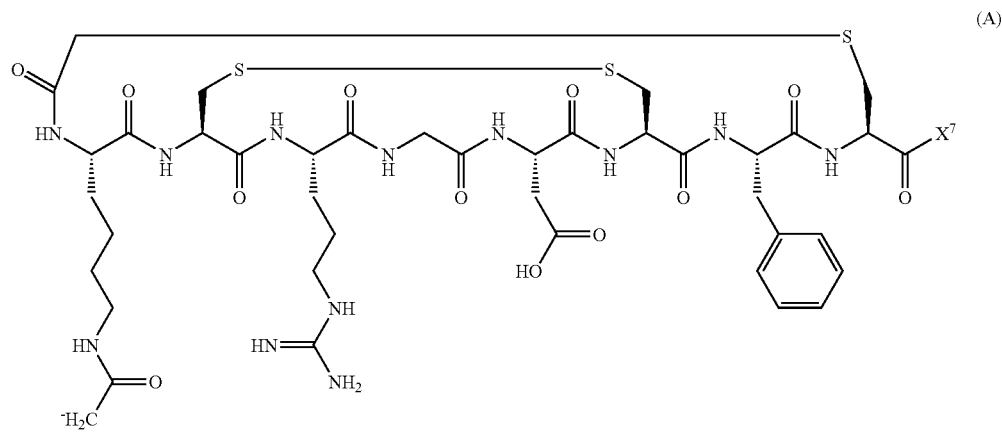

(A)

wherein X⁷ is either —NH₂ or

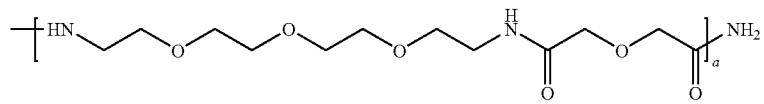

wherein a is an integer of from 1 to 10, preferably a is 1.

In a further aspect the present invention provides radiolabelled conjugates of formulae (V) and (VI), as well as the compounds of formulae (Va), (VIa), (XII), (XIII), (XIV), (XV), (XXI), (XXII), (XXIII), (XXIV); all as defined above. Preferred compounds of formulae (V), (VI), (Va), (VIa), (XII), (XIII), (XIV), (XV), (XXI), (XXII), (XXIII), and (XXIV) are those wherein the vector is Arg-Gly-Asp peptide or an analogue thereof as described above, and especially where the vector is of formula (A):

Compounds of formula (II) may be prepared from the corresponding precursors of formula (XXV):

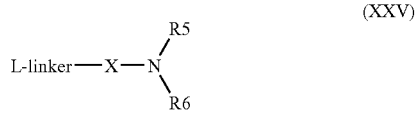

(XXV)

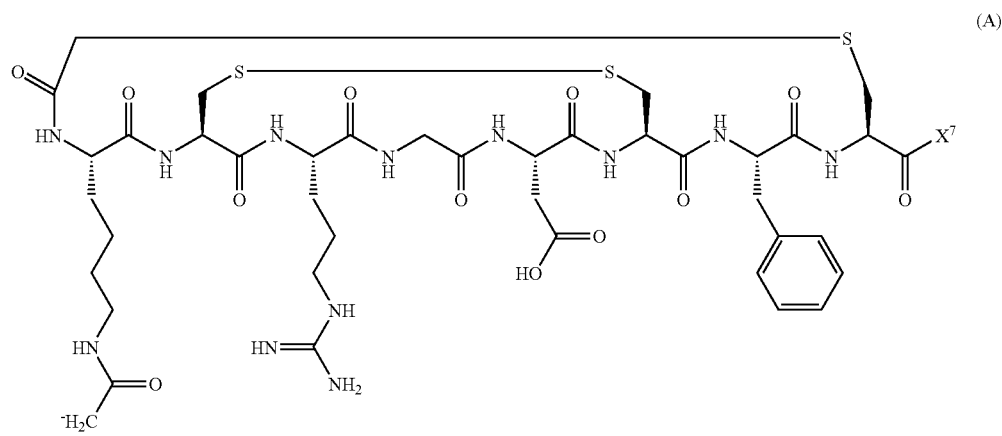

(A)

wherein X⁷ is either —NH₂ or

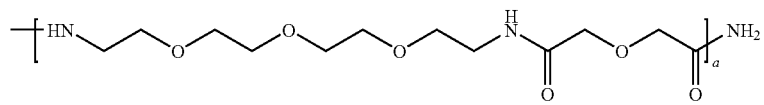

wherein a is an integer of from 1 to 10, preferably a is 1.

wherein L is a leaving group preferably a p-toluenesulphonate, trifluoromethanesulphonate, or methanesulphonate or a halide and the Linker is as defined previously and where X is preferably —CO—NH—, —NH— or —O—, R5 and R6 are either H or a suitable protecting group such as the t-butyloxycarbonyl by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at ambient or at elevated temperature, for example up to 150° C., suitably 60 to 120° C. or by microwave heating, followed by removal of any N-protecting group using standard methods such as acidolytic treatment.

Compounds of formula (IV) may be prepared from the corresponding precursors of formula (XXVI):

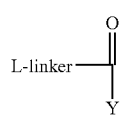

(XXVI)

or a protected derivative thereof, wherein L is a leaving group preferably a p-toluenesulphonate, trifluoromethanesulphonate, or methanesulphonate or a halide and the Linker is as defined previously and Y is preferably H, alkyl or aryl substituents by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at ambient or at elevated temperature, for example up to 120° C. The aldehyde or ketone function of compounds of formula (XXVI) can also be rapidly generated from their protected precursors such as acetals or ketals by simple acid treatment following fluorination. In a preferred example compounds of the formula (IV) are prepared from compounds of formula (XXVII)

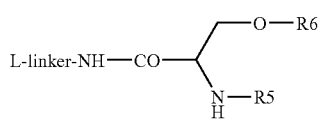

(XXVII)

wherein L is a leaving group such as p-toluenesulphonate, trifluoromethanesulphonate, methanesulphonate, or a halide, and the linker is defined as above and is joined via an amide bond to a protected serine derivative. In this case the O-protecting group R6 is preferably t-butyl and R5 is defined as above. Reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at ambient or at elevated temperature, for example up to 150° C., suitably 60 to 120° C. or my microwave heating, followed by removal of O and N-protection and oxidation to the aldehyde by an oxidising agent such as periodate.

In one preferred aspect, the compounds of formulae (IV) may be prepared on a solid support, such as polymer beads, coatings or micro-scale devices, for example, on a resin using a BAL strategy as described by Brask et al in Bioorg. Med. Chem. Left. 11 (2001) 697-700 The peptide aldehydes are synthesised starting with a reductive amination of O-PALaldehyde on PEG-AMPS resin with aminoacetaldehyde dimethyl acetal followed by acylation with the linker component. In this aspect, excess reagents and by-products from the radio-fluorination reaction may be separated from the polymer-bound product by washing. By acid treatment compounds of formula (IV) are obtained directly from the solid-support as shown below.

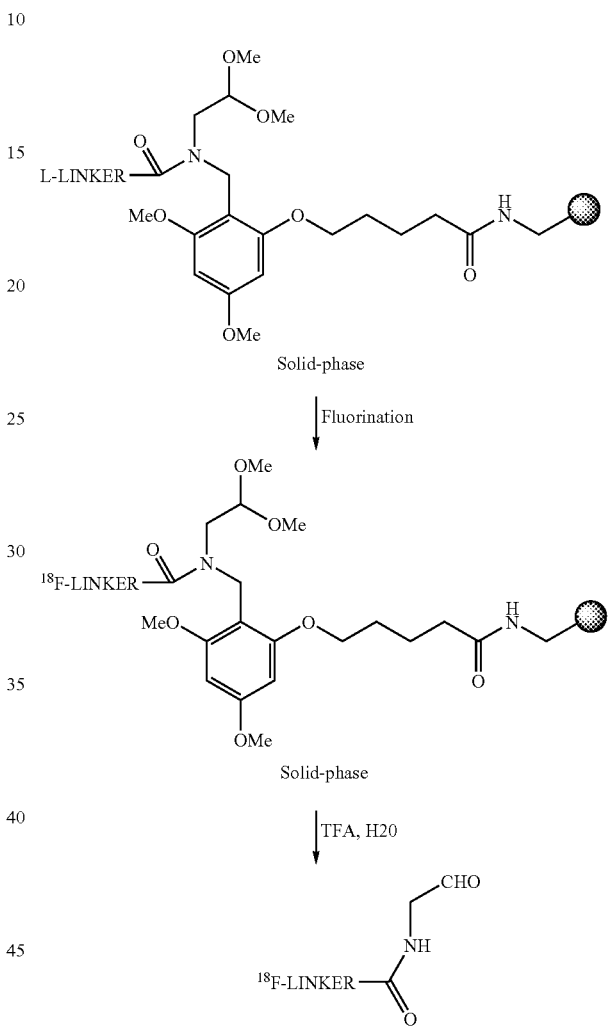

wherein L and linker are as described above.

This approach may be particularly suitable for automated production of the compounds of formulae (IV).

The present invention also provides a radiopharmaceutical composition comprising an effective amount (e.g. an amount effective for use in in vivo PET imaging) of a compound of general formula (V) or (VI), or a compound of formula (Va), (VIa), (XII), (XIII), (XIV), (XV), (XXI), (XXII), (XXIII), or (XXIV); all as defined above; together with one or more pharmaceutically acceptable adjuvants, excipients or diluents.

A preferred embodiment of the invention relates to a compound of general formula (V) or (VI), or a compound of formula (Va), (VIa), (XII), (XIII), (XIV), (XV), (XXI), (XXII), (XXIII), or (XXIV); all as defined above, for medical use and particularly for use in tumour imaging (suitably by PET); wherein the vector is Arg-Gly-Asp peptide or an analogue thereof, such as those described in WO 01/77415 and WO 03/006491, preferably a peptide comprising the fragment

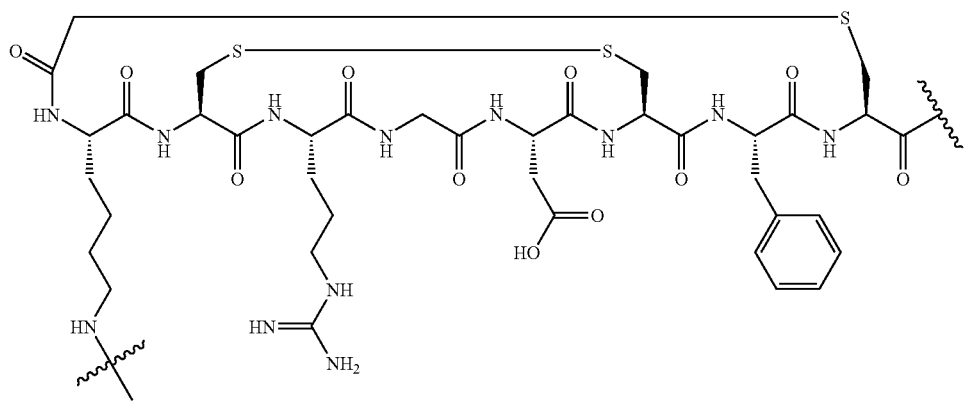

more preferably the peptide of formula (A):

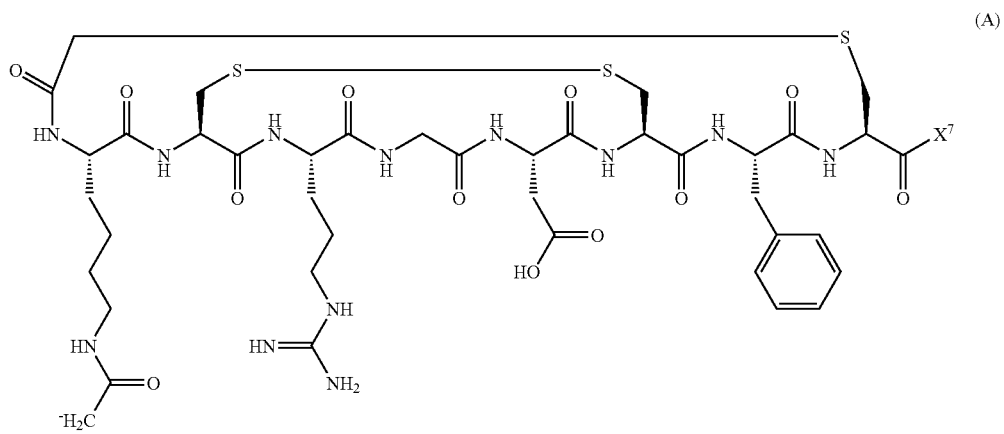

wherein $X^7$ is either —$NH_2$ or

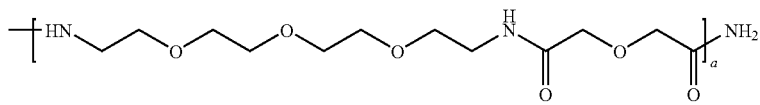

wherein a is an integer of from 1 to 10, preferably a is 1.

The radiolabelled conjugates of the invention may be administered to patients for PET imaging in amounts sufficient to yield the desired signal, typical radionuclide dosages of 0.01 to 100 mCi, preferably 0.1 to 50 mCi will normally be sufficient per 70 kg bodyweight.

The radiolabelled conjugates according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Viewed from a further aspect the invention provides the use of a radiolabelled conjugate of the invention for the manufacture of a radiopharmaceutical for use in a method of in vivo imaging, suitably PET, and preferably for tumour imaging; involving administration of said radiopharmaceutical to a human or animal body and generation of an image of at least part of said body.

Viewed from a still further aspect the invention provides a method of generating an image of a human or animal body involving administering a radiopharmaceutical to said body, e.g. into the vascular system and generating an image of at least a part of said body to which said radiopharmaceutical has distributed using PET, wherein said radiopharmaceutical comprises a radiolabelled conjugate according to the invention.

Viewed from a further aspect the invention provides a method of monitoring the effect of treatment of a human or animal body with a drug to combat a condition associated with cancer, preferably angiogenesis, e.g. a cytotoxic agent, said method comprising administering to said body a radiolabelled conjugate according to the invention and detecting the uptake of said conjugate by cell receptors, preferably endothelial cell receptors and in particular αvβ3 receptors, said administration and detection optionally but preferably being effected repeatedly, e.g. before, during and after treatment with said drug.

In yet another embodiment of the instant invention, there is provided a kit for the preparation of a radiofluorinated tracer comprising a prosthetic group of formula (II) or (IV) and a compound of formula (I) or (III).

According to a further aspect of the invention, there is provided a kit for the preparation of a radiofluorinated tracer comprising a prosthetic group of formula (XXV) and a compound of formula (I). According to another aspect of the invention, there is provided a kit for the preparation of a radiofluorinated tracer comprising a prosthetic group of formula (XXVI) or (XXVII), and a compound of formula (III).

In use of the kits, the compound of formula (XXV) would be converted to the corresponding compound of formula (II) and the compound of formula (XXVI) or (XXVII) would be converted to the corresponding compound of formula (IV), respectively, using methods described above. Preferably, the compound of formula (II) and (IV) may be separated from waste reactants by passing the reaction mixture through a Solid Phase Extraction (SPE) cartridge. The SPE cartridge may comprise a graphite pad, $C_{18}$ stationary phase or ion exchange resin. The compound of formula (II) and (IV) would then be added to the compounds of formula (I) and (III) respectively which may suitably be dissolved in aqueous buffer (pH 3-11). After reaction at a non-extreme temperature for 1 to 70 minutes, the labelled peptide may be purified, for example, by SPE and collected.

EXAMPLES

The invention is illustrated by way of examples in which the following abbreviations are used:

| | |
|---|---|
| HPLC: | high performance liquid chromatography |
| NMR: | nuclear magnetic resonance |
| TFA: | trifluoroacetic acid. |
| hr(s): | hour(s) |
| min(s): | minute(s) |
| DMAP: | 4-(dimethylamino)pyridine |
| THF: | tetrahydrofuran |
| DCM: | dichloromethane |
| DMF: | N,N-dimethylformamide |
| TBAF: | tetrabutylammonium fluoride |
| MeOH: | methanol |
| TLC: | thin layer chromatography |
| TIS: | triisopropylsilane |
| DMSO: | dimethylsulphoxide |
| PyAOP: | [7-azabenzotriazol-1-yloxytris(pyrrolidino)phosphonium-hexafluorophosphate] |
| Boc: | t-butoxycarbonyl |

Example 1

Preparation of 4-trimethylammonium benzaldehyde triflate (compound 1)

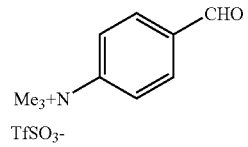

This compound was synthesised according to the procedure described by Haka et al (J. Labelled Cpds. & Radiopharms 1989 27(7) 823).

Example 2

Preparation of 2-(2-{2-[2-(2-fluoro-ethoxy)-ethoxy]-ethoxy}-ethoxy)-1,1-dimethoxy-ethane (compound 7)

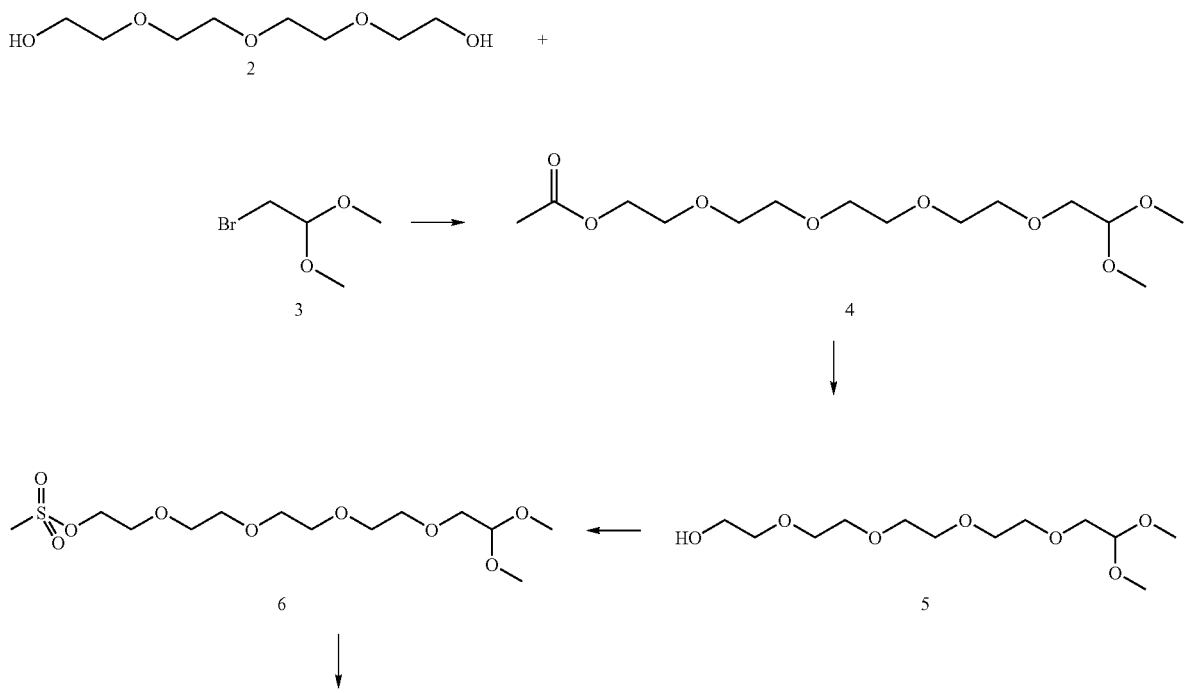

-continued

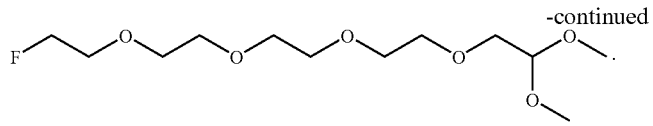

7 a) Acetic acid 2-(2-{2-[2-(2,2-dimethoxy-ethoxy)-ethoxy]-ethoxy}-ethoxy)-ethyl ester (Compound 4)

To a stirring suspension of sodium hydride (248 mg, 5.15 mmol in mineral oil) in THF (5 ml) was added through a syringe a solution of 2-{2-[2-(2-hydroxy-ethoxy)-ethoxy]-ethoxy}-ethanol (Compound 2) (1.0 g, 5.15 mmol) in THF (5 ml) at ambient temperature. After gas evolution had ceased, the mixture was stirred for 45 minutes at room temperature by which time a clear slightly yellow solution was obtained. Bromoacetaldehyde (8.71 g, 51.5 mmol) was added via syringe and the mixture stirred for 24 hours. Then ethyl acetate was (3 ml) was added and the mixture stirred at ambient temperature a further 2 hours. The mixture was poured into ether (100 ml) and extracted once each with 10% aqueous $K_2CO_3$ (30 ml) and brine (30 ml). The organic phase was dried ($Na_2SO_4$, filtered and evaporated. The residual oil was distilled to eliminate excess bromoacetaldehyde and the residual crude product was purified by flash chromatography using 100% ethyl acetate to afford the product (355 mg, 21%) as a colourless oil.

b) 2-(2-{2-[2-(2,2-Dimethoxy-ethoxy)-ethoxy]-ethoxy}-ethoxy)-ethanol (Compound 5)

1 N NaOH/Methanol (1 ml) was added to a stirring solution of acetic acid 2-(2-{2-[2-(2,2-dimethoxy-ethoxy)-ethoxy]-ethoxy}-ethoxy)-ethyl ester (Compound 4) (110 mg, 0.34 mmol) in methanol (3 ml) at ambient temperature. The reaction was monitored by TLC ($CHCl_3$/MeOH, 9:1) and was completed within 30 minutes. The solvent was evaporated and the residue purified by flash chromatography ($CHCl_3$/MeOH, 9:1) to afford the product (73 mg, 76%) as a colourless oil.

c) Methanesulfonic acid 2-(2-{2-[2-(2,2-dimethoxy-ethoxy)-ethoxy]-ethoxy}-ethoxy)-ethyl ester (Compound 6)

To a stirring solution of the alcohol (Compound 5) (60 mg, 0.21 mmol) and triethylamine (59 µl, 0.42 mmol) in THF (1 ml) was added methanesulfonyl chloride (24:1, 0.30 mmol). The reaction was monitored by TLC ($CHCl_3$/MeOH, 9:1). After 2 hours the precipitated triethylamine hydrochloride salt was filtered off. The solvent was evaporated and the product (75 mg, 99%) obtained after flash chromatography using chloroform/methanol (9:1) as oil.

d) 2-(2-{2-[2-(2-Fluoro-ethoxy)-ethoxy]-ethoxy}-ethoxy)-1,1-dimethoxy-ethane (Compound 7)

A mixture of the sulfonate (Compound 6) (75 mg, 0.21 mmol) and TBAF (1.1 M in THF, 573 µl, 0.63 mmol) in acetonitrile (8 ml) was heated at 90° C. for 30 minutes. TLC (ethyl acetate) monitoring showed the reaction was completed. After cooling to ambient and evaporation of the solvent the residue was flashed (Ethyl acetate) to afford the product (56 mg, 93%) as colourless oil.

Example 3

Preparation of 4-(3-fluoropropoxy)benzaldehyde (Compound 10)

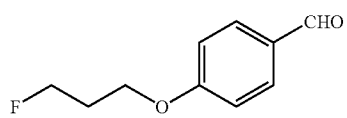

a) 4-(3-hydroxyethoxy)benzaldehyde (Compound 8)

A solution of 4-hydroxybenzaldehyde (Fluka, 4.9 g, 0.040 mol), sodium carbonate (4.7 g, 0.044 mol) and 3-bromo-1-propanol (6.1 g, 0.044 mol) in DMF (30 ml) was heated at 140° C. for 8 hrs. The reaction mixture was cooled and concentrated and the residue was taken up in ether, washed with water and dried ($Na_2SO_4$). Filtration and concentration gave 4.6 g (64%) of a yellow syrup that was used in the next step without further purification. The structure was confirmed by NMR analysis.

b) Methanesulphonic acid 3-(4-formylphenoxy)ethyl ester (Compound 9)

To a solution of the alcohol 12 (1.4 g, 8.0 mmol) in dichloromethane (10 ml) was added triethylamine (1.2 ml, 8.5 mmol) and mesyl chloride (0.62 ml, 8.0 mmol). After stirring for 1.5 hrs at room temperature the reaction mixture was washed with water and dried ($Na_2SO_4$) to give 1.8 g of crude material (yellow oil). An aliquot of 290 mg was purified by reverse phase chromatography (column Phenomenex Luna C18(2) 5 µm 21.2×250 mm, solvents: A=water/0.1% TFA and B=acetonitrile/0.1% TFA; gradient 20-40% B over 60 min; flow 10.0 ml/min, UV detection at 254 nm) to give 244 mg of white, solid material after lyophilisation. The structure was confirmed by NMR analysis.

c) 4-(3-fluoropropoxy)benzaldehyde (Compound 10)

Potassium fluoride (Fluka, 7.2 mg, 0.124 mmol) and kryptofix 222 (Fluka, 46.7 mg, 0.124 mmol) were dissolved in dry acetonitrile (2.5 ml). After 10 min the mixture was added to a stirred solution of methanesulfonic acid 3-(4-formylphenoxy)propyl ester 13 (16.0 mg, 0.062 mmol) in dry acetonitrile (1.5 ml). The reaction mixture was heated at 60° C. for 30 minutes. The product was confirmed by analytical HPLC (column Phenomenex Luna C18(2) 3 µm 4.6×50 mm, solvents: A=water/0.1% TFA and B=acetonitrile/0.1% TFA; gradient 10-80% B over 10 min; flow 2.0 ml/min, UV detection at 214 and 254 nm) co-eluting with commercial standard (Fluorochem) at 5.0 minutes.

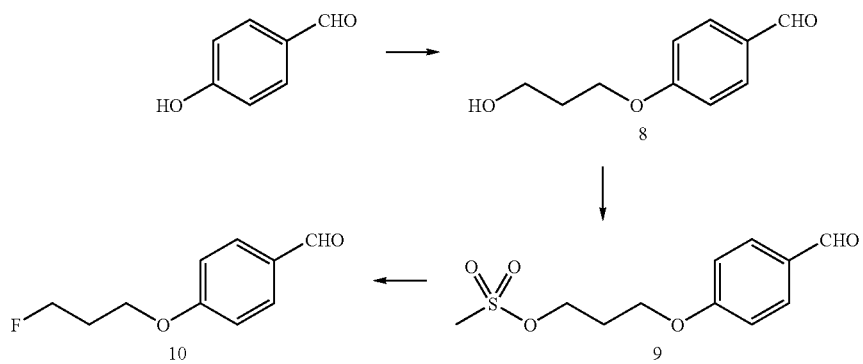

Example 4

Preparation of 1,1 Dimethoxy-4-fluoromethyl cyclohexane (Compound 14)

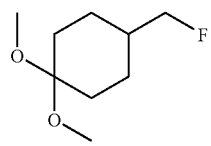

a) 4-Hydroxymethyl cyclohexanone (Compound 11)

This compound was synthesised according to the procedure described by Borden et. al (J. Org. Chem., 1985, 50, 531-534. The product was characterised by 1H and 13C NMR.

b) 1,1-dimethoxy-4-hydroxymethyl cyclohexane (Compound 12)

A solution of ketone 11 (2.54 g, 19.8 mmol), trimethyl orthoformate (9.75 ml, 89.1 mmol) and p-toluene sulphonic acid (150 mg, 0.79 mmol) in dry methanol (30 ml) was stirred under nitrogen at room temperature for 24 hrs. The reaction mixture was neutralized with solid potassium carbonate (4 g), filtered and the solvents evaporated. The crude was dissolved in DCM (30 ml) and washed with water (40 ml). The organic phase was dried ($Na_2SO_4$), filtered and evaporated. The crude yellow oil (3.0 g) was distilled at 85 C (0.2 mmHg) to afford the product (1.69 g, 49%) as a colourless oil. The product was characterised by 1H and 13C NMR.

c) Methanesulfonic acid 4,4-dimethoxy-cyclohexylmethyl ester (Compound 13)

To a cooled (0 C) solution of the alcohol 12 (275 mg, 1.58 mmol) and triethylamine (3.3 ml, 23.7 mmol) in dry DCM (5 ml) under nitrogen was added dropwise methanesulphonyl chloride (246 ul, 3.16 mmol). The reaction mixture was stirred at room temperature for 2 hours. The precipitated triethylamine hydrochloride salt was filtered off and the solvents evaporated. The crude was dissolved in DCM (30 ml), washed with water (2×20 ml), dried ($Na_2SO_4$), filtered and evaporated. The residue was purified by flash chromatography (EtOAc: pet. Spirit: $NH_3$ (50:50:4) to afford the product (214 mg, 54%) as a pale yellow oil. The product was characterised by 1H and 13C NMR.

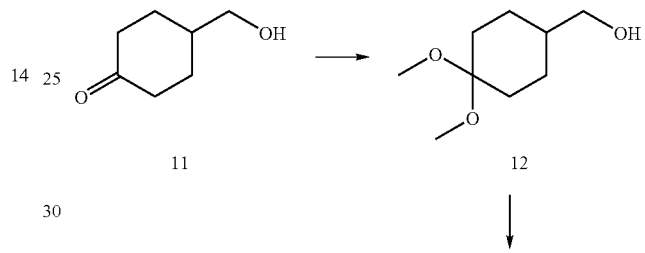

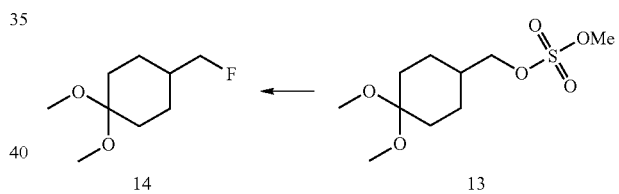

Example 5

Preparation of Peptide Precursor (Compound 15)

The peptide, Compound 14 was synthesised using standard peptide synthesis. Compound 14 (150 mg, 0.12 mmol) in DMF was added to a solution of Boc-aminoxyacetic acid (34.4 mg, 0.18 mmol), PyAOP (93.9 mg, 0.18mmol) and NMM (40 µl, 0.36 mmol) in DMF. DMF was evaporated under reduced pressure after 12 hours and the crude product was purified by reverse phase preparative chromatography (Phenomenex Luna C18 column, 00G-4253-V0; solvents A=water/0.1% TFA and B=$CH_3CN$/0.1% TFA; gradient 10-50% B over 60 min; flow 50 ml/minute; detection at 254 nm), affording 97.1 mg (57%) of pure compound (analytical HPLC: Phenomenex Luna C18 column, 00G-4252-E0; solvents: A=water+0.1% TFA/B=$CH_3CN$+0.1% TFA, gradient: 10-50% B over 20 min; flow 1.0 ml/minute; retention time 19.4 minutes, detected at 214 and 254 nm). Further characterisation was carried out using mass spectrometry, giving m/z value 1431.2 [M–H$^+$].

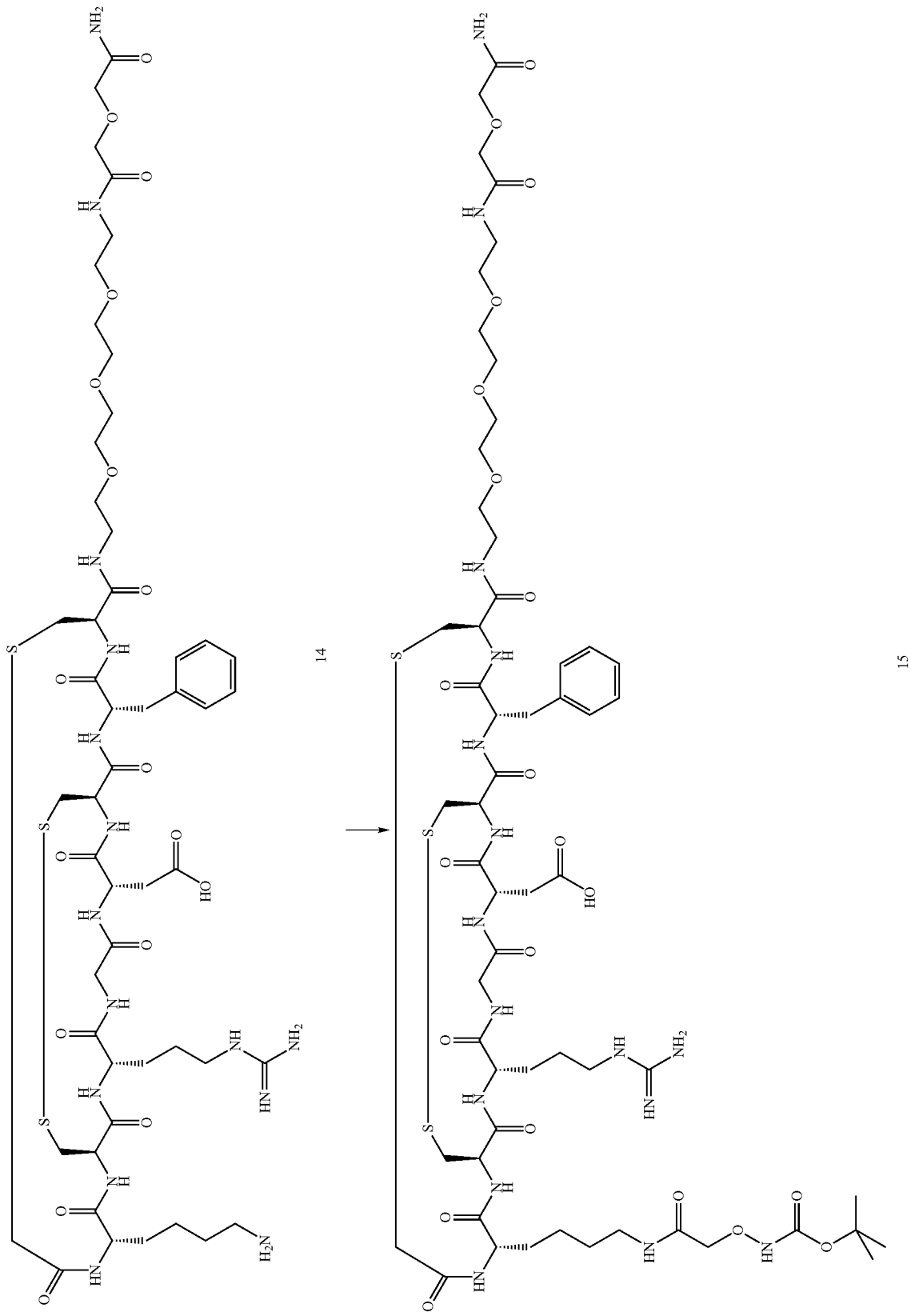

Example 6

Chemoselective ligation of Compound 1 to Compound 15 to give Compound 16

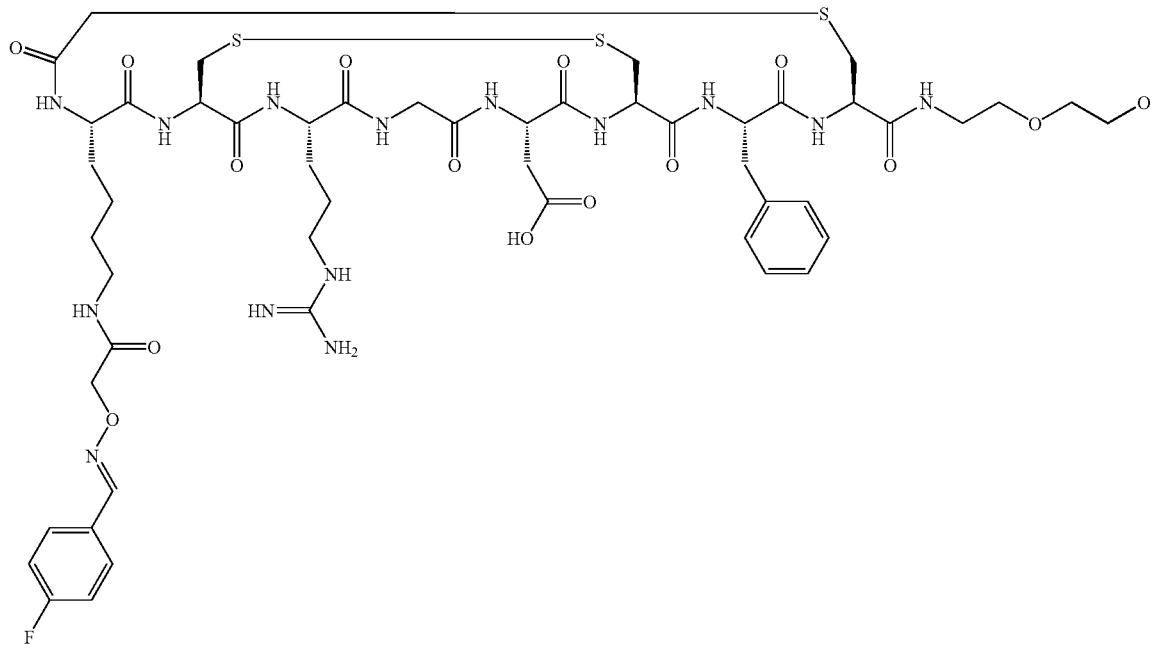

16

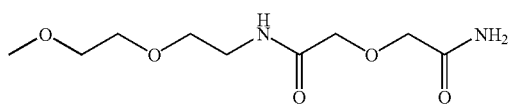

Deprotection of peptide 15 was carried out by addition of TFA containing 5% water to 10 mg of peptide. The Boc-deprotected peptide (5.9 mg, 0.0044 mmol) in 1 ml water was added to 4-fluoro benzaldehyde (Compound 1) (1.1 mg, 0.94 µl, 0.0089 mmol) in 1 ml acetonitrile. pH of the mixture was 3.5. After 45 minutes at 70 degrees the mixture was purified by reverse phase preparative chromatography twice (Phenomenex Luna C18 column, 00G-4253-N0; solvents: A=water+0.1% TFA/B=CH$_3$CN+0.1% TFA, gradient: 10-40% B over 30 min; flow 5.0 ml/minute; detected at 214 nm), affording 2.0 mg (32%) of pure compound (analytical HPLC: Phenomenex Luna C18 column, 00G-4252-E0; solvents: A=water+0.1% TFA/B=CH$_3$CN+0.1% TFA, gradient: 10-50% B over 20 min; flow 1.0 ml/minute; retention time 16.3 minutes, detected at 214 and 254 nm). Further characterisation was carried out using mass spectrometry, giving m/z value 1437.2. [M−H$^+$].

Example 7

Chemoselective ligation of Compound 7 to Compound 15 to give Compound 17

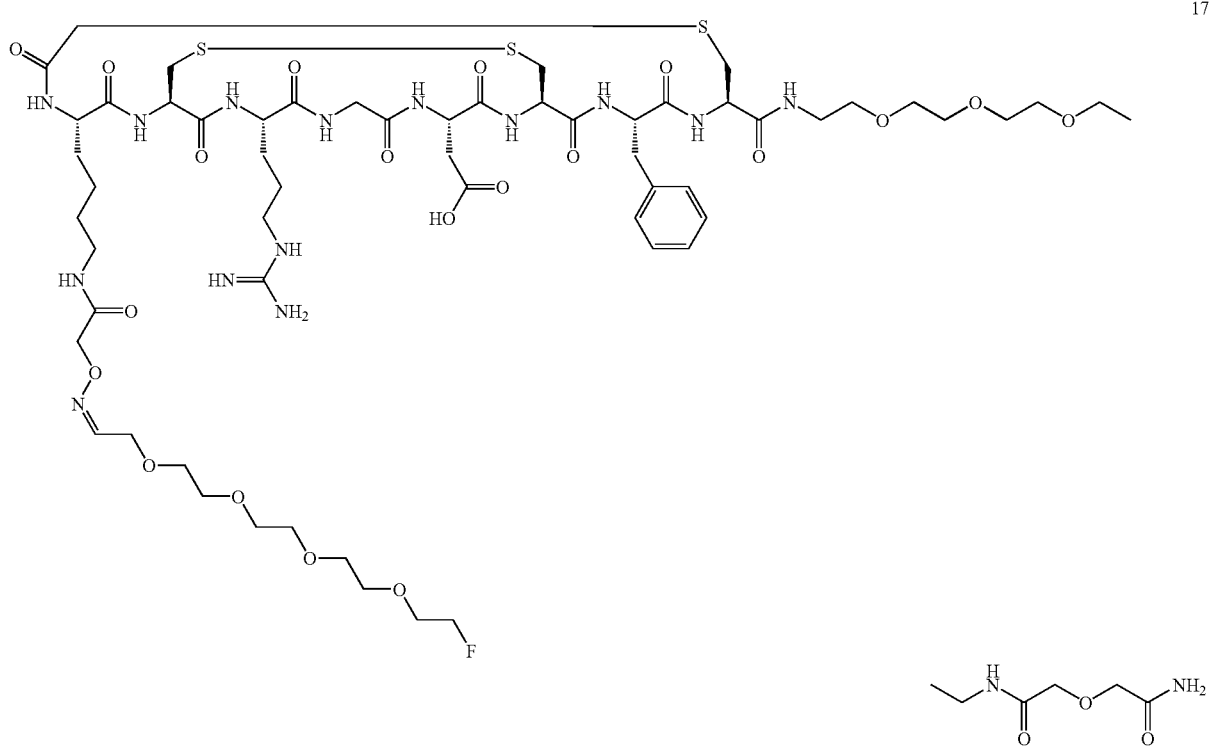

The protecting group on 2-(2-{2-[2-(2-fluoro-ethoxy)-ethoxy]-ethoxy}-ethoxy) 1,1-dimethoxy ethane 6 (3.9 mg, 0.016 mmol) was removed using HCl (cons.) in acetonitrile (1:1) (0.5 ml). The mixture was left for 15 minutes and then added to the Boc-deprotected peptide, obtained by treating (Compound 9) (10 mg, 0.007 mmol) with TFA containing 5% water and then evaporating TFA under reduced pressure after 20 min. The pH of the mixture was adjusted to 4 with ammonia and then heated to 70 degrees for 20 minutes. The reaction was monitored using analytical HPLC and LC-MS and purified by reverse phase preparative chromatography (Phenomenex Luna C18 column, 00G-4253-N0; solvents: A=water+ 0.1% TFA/B=CH$_3$CN+0.1% TFA, gradient: 10-50% B over 30 min; flow 5.0 ml/minute; detected at 214 nm), affording 5.5 mg (51%) of pure compound (analytical HPLC: Phenomenex Luna C18 column, 00G-4252-E0; solvents: A=water+ 0.1% TFA/B=CH$_3$CN+0.1% TFA, gradient: 10-50% B over 20 min; flow 1.0 ml/minute; retention time 14.3 and 14.7 minutes, detected at 214 and 254 nm). Further characterisation was carried out using mass spectrometry, giving m/z value 1551.1. [M–H$^+$].

Example 8

Radiosynthesis of $^{18}$F-compound 16 a) Radiosynthesis of $^{18}$F-Compound 1

$^{18}$F-fluoride (up to 370 MBq) was azeotropically dried in the presence of Kryptofix 222 (12-14 mg in 0.5 ml MeCN) and potassium carbonate (100 µl 0.1M solution in water) by heating under N$_2$ to 125° C. for 15 mins. During this time 2×1 ml MeCN were added and evaporated. After cooling to <40° C., a solution of trimethylammonium benzaldehyde triflate (3-7 mg in 0.7 ml DMSO) was added. The reaction vessel was sealed and heated to 120° C. for 15 mins to effect labelling. The crude reaction mixture was cooled to room temperature and diluted by addition to 10 ml water. The mixture was passed sequentially through a Sep-pak CM-plus cartridge (conditioned with 10 ml water) and a SepPak C18-plus cartridge (conditioned with 20 ml EtOH and 20 ml H$_2$O). The cartridges were flushed with water (10 ml), and the product $^{18}$F-fluorobenzaldehyde was eluted from the SepPak C18-plus cartridge with MeOH (1 ml).

b) Conjugation of Compound 15 and 4-$^{18}$F-fluorobenzaldehyde

Compound 15 (4-5 mg) was treated with 5% water in TFA for 5 mins at room temperature. The solvents were then removed by evaporation under vacuum. The peptide was redissolved in 0.5M NH$_4$OAc buffer, pH4 (0.5 ml) and combined with 4-$^{18}$F-fluorobenzaldehyde in the reaction vessel. The reaction vessel was sealed and heated to 70° C. for 15 mins to effect conjugation. After cooling to room temperature, the product was obtained by preparative radio HPLC (Column Phenomenex Prodigy ODS-Prep, 250×10 mm, 10µ, 4 ml/min, solvent A: H$_2$O (0.5% TFA), solvent B: CH$_3$CN (0.5% TFA), gradient: 10% B for 5 mins, 10-40% B in 15 min).

Example 9

Radiosynthesis of $^{18}$F-compound 17 a) Radiosynthesis of $^{18}$F Compound 7

To a Wheaton vial (2 ml) charged with Kryptofix 222 (10 mg), potassium carbonate (1 mg in 50 µl water), and acetonitrile (0.8 ml) the fluorine-18 containing water (10 mCi, 1 ml) were added. The solvent was removed by heating at 110° C. for 30 min under a stream of nitrogen. Anhydrous acetonitrile (0.5 ml) was added and evaporated as before. This step was repeated twice. A solution of compound 6 (1 mg) in anhydrous DMSO (0.2 ml) was added. After heating by microwave (5 min, 160° C., 150→50 W) the reaction mixture was cooled to room temperature and applied to a SepPak 'C18-plus cartridge that had been conditioned with MeCN (5 ml) and H$_2$O (20 ml). The cartridge was flushed with water (10 ml), and the product eluted with MeCN (0.5 ml). The solvent was evaporated using a stream of nitrogen at 80° C. A mixture of HCl (34 µl, 12 M) and MeCN (34 µl) was added and the vial left at room temperature for 5 min.

b) Conjugation of Compound 15 and $^{18}$F—Compound 7

Compound 15 (3 mg) was reacted with TFA/5% H$_2$O (0.2 ml). After standing for 1 min at room temperature the solvent was removed by a stream of nitrogen. Ammonium hydroxide (38 µl, 28%) was added to the vial containing deprotected $^{18}$F-compound 7. The neutralised mixture was transferred into the vial containing deprotected compound 15 in ammonium acetate buffer (50 µl, pH 4.0, 0.5 M). The vial was incubated at 70° C. for 7 min. After cooling to room temperature and adding of HPLC mobile phase (100 µl, 20% MeCN, 80% H$_2$O, 0.5% TFA) the product was obtained by preparative radio HPLC [column: Luna C18(2), Phenomenex, 100× 10 mm, 5 µ, 4 ml/min, solvent A: H$_2$O (0.5% TFA), solvent B: CH$_3$CN (0.5% TFA), gradient: 10-50% B in 20 min].

Example 10

Synthesis of 4-(fluoromethyl)benzoyllhydrazide—Compound 23

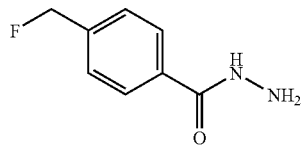

23

Preparation of tri-tert-butyl 2-[4-(fluoromethyl)benzoyl]hydrazino-1,1,2-tricarboxylate for conjugation with aldehyde or ketone modified peptides a) Synthesis of tert-butyl 2-[4-(hydroxymethyl)benzoyl]-hydrazino-1-carboxylate—Compound 18

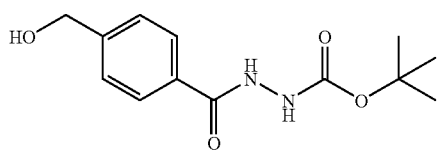

18

A solution of 4-hydroxymethyl benzoic acid pentafluorophenyl ester (Milligen, 0.60 g, 1.9 mmol), hydroxybenzotriazole (0.29 g, 1.9 mmol), tert-butyl carbazate (Fluka, 0.29 g, 2.2 mmol) and diisopropylethylamine (0.68 ml, 4.0 mmol) in dichloromethane (20 ml) was refluxed for 3 hours. The reaction mixture was concentrated in vacuo and the product was purified by column chromatography (silica, ethyl acetate/hexane 9:1). Yield 0.50 g (90%). Analytical HPLC: column Phenomenex Luna C18(2) 3 µm 4.6×50 mm; solvents: A=water/0.1% TFA and B=acetonitrile/0.1% TFA; gradient 10-80% B over 10 min; flow 2.0 ml/min; retention time 2.38 minutes detected at 214 and 254 nm. NMR analysis was in accordance with the structure.

b) Synthesis of tert-butyl 2-[4-(tert-butyldiphenylsiloxymethyl)benzoyl]hydrazino-1-carboxylate—Compound 19

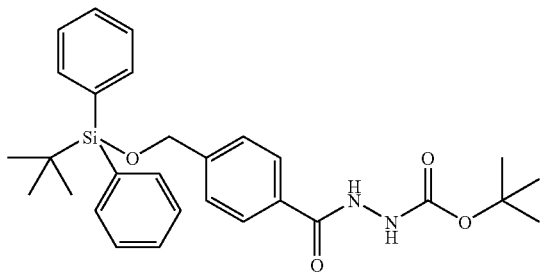

19

A solution of tert-butyldiphenylchlorosilane (0.57 ml, 2.2 mmol), tert-butyl 2-[4-(hydroxymethyl)benzoyl]-hydrazino-1-carboxylate (0.48 g, 1.8 mmol) and imidazole (0.37 g, 5.4 mmol) in dichloromethane (60 ml) was stirred at room temperature for 1 hr 15 min. The solution was extracted with aqueous potassium hydrogensulphate (pH3, 3×20 ml) and dried (Na$_2$SO$_4$). The product was analysed by HPLC (column Phenomenex Luna C18(2) 3 µm 4.6×50 mm; solvents: A=water/0.1% TFA and B=acetonitrile/0.1% TFA; gradient 60-100% B over 10 min; flow 2.0 ml/min; retention time 3.37 minutes detected at 214 and 254 nm). The solution was concentrated and the product was used in the next step without further purification.

c) Synthesis of tri-tert-butyl 2-[4-(tert-butyldiphenylsiloxymethyl)benzoyl]hydrazino-1,1,2-tricarboxylate—Compound 20

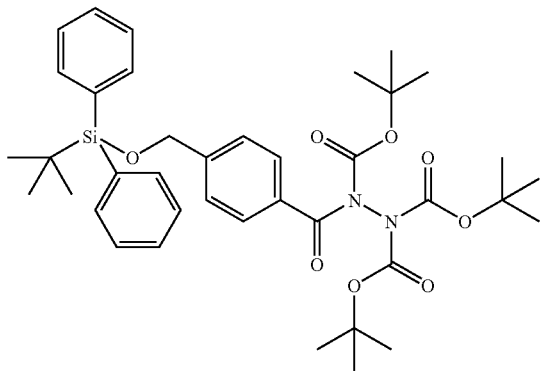

20

To a solution of tert-butyl 2-[4-(tert-butyldiphenylsiloxymethyl)benzoyl]hydrazino-1-carboxylate (69 mg, 0.14 mmol) in dichloromethane (15 ml) were added DMAP (20 mg, 0.16 mmol), triethylamine (0.13 ml, 0.96 mmol) and di-tert-butyl-dicarbonate (90 mg, 0.41 mmol). After 2 hours the solvent was evaporated under reduced pressure and crude product was purified by column chromatography (silica, hexane/ethyl acetate, 4:1 (analytical HPLC: column Phenomenex Luna C18(2) 3 µm 4.6×50 mm; solvents: A=water/0.1% TFA and B=acetonitrile/0.1% TFA; gradient 60-100% B over 10 min; flow 2.0 ml/min; retention time 7.85 minutes detected at 214 and 254 nm). The structure was confirmed by NMR analysis.

d) Synthesis of tri-tert-butyl 2-[4-(hydroxymethyl)benzoyl]hydrazino-1,1,2-tricarboxylate—Compound 21

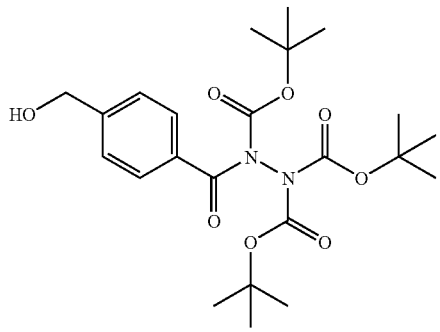

21

To a solution of tri-tert-butyl 2-[4-(tert-butyldiphenylsiloxymethyl)benzoyl]hydrazino-1,1,2-tricarboxylate (0.37 g, 0.52 mmol) in THF (25 ml) was added tetrabutylammonium fluoride (1.1 M in THF, 0.50 ml, 0.55 mmol). After 50 min aqueous ammonium chloride solution (10%, 10 ml) was added. After 10 min the mixture was extracted with dichloromethane (3×15 ml) and the organic phase was dried (Na$_2$SO$_4$). The solution was concentrated and the residue was purified by column chromatography (silica, hexane/ethyl acetate 1:1) to give 0.21 g (84%) of product (analytical HPLC: column Phenomenex Luna C18(2) 3 µm 4.6×50 mm; solvents: A=water/0.1% TFA and B=acetonitrile/0.1% TFA; gradient 60-100% B over 10 min; flow 2.0 ml/min; retention time 1.38 min detected at 214 and 254 nm). The structure was confirmed by NMR analysis.

e) Synthesis of tri-tert-butyl 2-[4-(methanesulfonatomethyl)benzoyl]hydrazino-1,1,2-tricarboxylate—Compound 21

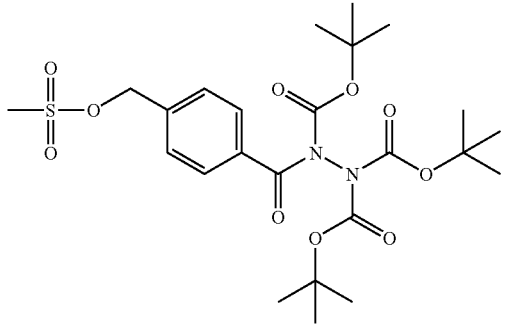

21

To a stirred solution of tri-tert-butyl 2-[4-(hydroxymethyl)benzoyl]hydrazino-1,1,2-tricarboxylate (0.22 g, 0.48 mmol) and triethylamine (0.080 ml, 0.57 mmol) in dichloromethane (40 ml) was added methanesulphonyl chloride (0.040 ml, 0.52 mmol). After 2 hrs a second portion of methanesulphonyl chloride and triethylamine (same amounts) was added. After 12 hours analytical HPLC (column Phenomenex Luna C18(2) 3 µm 4.6×50 mm; solvents: A=water/0.1% TFA and B=acetonitrile/0.1% TFA; gradient 10-80% B over 10 min; flow 2.0 ml/min; retention time 8.25 minutes by detection at 214 and 254 nm) indicated that the reaction was completed. The mixture was filtered through silica and concentrated in vacuo. The product was purified by column chromatography (silica, hexane/ethyl acetate 1:1), yield 0.21 g (81%). NMR analysis was in accordance with the structure.

f) Synthesis of tri-tert-butyl 2-[4-(flouromethyl)benzoyl]hydrazino-1,1,2-tricarboxylate—Compound 22

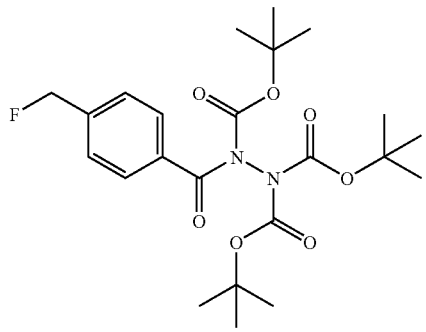

22

Potassium fluoride (3.0 mg, 0.052 mmol) and Kryptofix 222 (Fluka, 20 mg, 0.053 mmol) were dissolved in dry acetonitrile (0.6 ml). After 15 min the mixture was added to a stirred solution of tri-tert-butyl 2-[4-(methanesulfonatomethyl)benzoyl]hydrazino-1,1,2-tricarboxylate (14 mg, 0.026 mmol) in dry acetonitrile (0.4 ml). The reaction mixture was heated at 60° C. for 15 min. The product was purified by preparative HPLC (column Phenomenex Luna C18(2) 5 µm 21.2×250 mm; solvents: A=water/0.1% TFA and B=acetonitrile/0.1% TFA; gradient 60-100% B over 60 min; flow 10.0 ml/min; retention time 33 minutes detected at 214 nm). Yield 3.2 mg (26%). Analytical HPLC: column Phenomenex Luna C18(2) 3 µm 4.6×50 mm; solvents: A=water/0.1% TFA and B=acetonitrile/0.1% TFA; gradient 10-80% B over 10 min; flow 2.0 ml/min; retention time 8.78 minutes detected at 214 and 254 nm. The structure was confirmed by NMR analysis. The deprotection of Compound 22 to yield Compound 23 was carried out in 50% TFA/DCM for 15 minutes.

Example 11

Preparation of 2-[2-(2-fluoromethyl-phenylsulfanyl)-ethyl]-[1,3]dioxolane for conjugation with aminoxy, hydrazine or hydrazide modified peptides—Compound 27

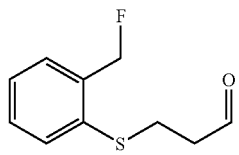

27 a) Synthesis of [2-(2-[1,3]dioxolan-2-ylethylsulfanyl)phenyl]methanol Compound 24

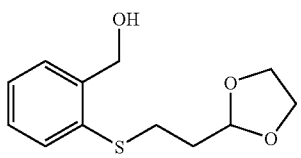

24

2-(2-Bromoethyl)-1,3-dioxolane (223 µl, 1.86 mmol) was added to 2-mercaptobenzyl alcohol (52.3 mg, 0.37 mmol) and potassium carbonate (102.3, 0.74 mmol) in DMF. The mixture was stirred at room temperature over night before DMF was evaporated under reduced pressure and the crude product purified by reverse phase preparative chromatography (Vydac 218TP1022 column; solvents A=water/0.1% TFA and B=CH$_3$CN/0.1% TFA; gradient 10-50% B over 40 min; flow 10 ml/minute; detection at 214 nm). A yield of 65.1 mg of purified material was obtained (Analytical HPLC: Vydac 218TP54 column; solvents: A=water/0.1% TFA and B=CH$_3$CN/0.1% TFA; gradient 10-50% B over 20 min; flow 1.0 ml/minute; retention time 15.017 minutes detected at 214 and 254 rim).

b) Synthesis of 2-[2-(2-chloromethyl-phenylsulfanyl)-ethyl]-[1,3]dioxolane—Compound 25

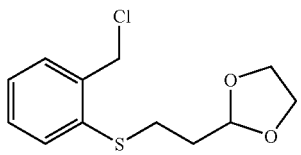

25

Mesyl chloride (65 µl, 0.83 mmol) was added to a solution of [2-(2-[1,3]dioxolan-2-yl-ethylsulfanyl)-phenyl]-methanol (40 mg, 0.17 mmol) and triethyl amine (116 µl, 0.83 mmol) in THF. After 5 days the precipitate was filtered of and THF evaporated under reduced pressure and the crude product purified by reverse phase preparative chromatography (Vydac 218TP1022 column; solvents A=water/0.1% TFA and B=CH$_3$CN/0.1% TFA; gradient 40-80% B over 40 min; flow 10 ml/minute; detection at 254 nm). The fractions were left in the fridge overnight and to the acetonitrile phase was added diethyl ether, dried (Na$_2$SO$_4$) and evaporated under reduced pressure. A yield of 24.5 mg of purified material was obtained (Analytical HPLC: Vydac 218TP54 column; solvents: A=water/0.1% TFA and B=CH$_3$CN/0.1% TFA; gradient 40-80% B over 20 min; flow 1.0 ml/minute; retention time 10.4 minutes detected at 214 and 254 nm). Structure verified by NMR.

c) Synthesis of 2-[2-(2-fluoromethyl-phenylsulfanyl)-ethyl]-[1,3]dioxolane—Compound 26

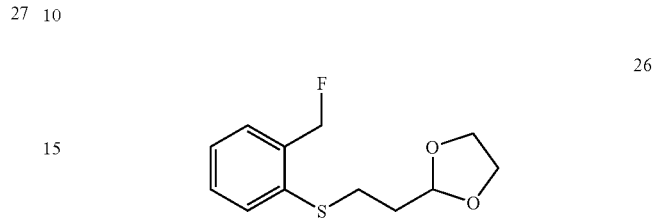

26

Potassium fluoride (3.5 mg, 0.060 mmol) and kryptofix 222 (22.5 mg, 0.060 mmol) were dissolved in acetonitrile (1 ml) and added to 2-[2-(2-chloromethyl-phenylsulfanyl)-ethyl]-[1,3]dioxolane (7.7 mg, 0.030 mmol) in acetonitrile (1 ml). The reaction mixture was heated to 70 degrees for 30 minutes. The crude product was purified by reverse phase preparative chromatography (Vydac 218TP1022 column; solvents A=water/0.1% TFA and B=CH$_3$CN/0.1% TFA; gradient 40-80% B over 40 min; flow 10 ml/minute; detection at 254 nm). The fractions were left in the fridge overnight and to the acetonitrile phase was added diethyl ether, dried (Na$_2$SO$_4$) and evaporated under reduced pressure. (Analytical HPLC: Vydac 218TP54 column; solvents: A=water/0.1% TFA and B=CH$_3$CN/0.1% TFA; gradient 40-80% B over 20 min; flow 1.0 ml/minute; retention time 9.200 minutes detected at 214 and 254 nm). Structure verified by NMR.

Example 12

Synthesis of 4-fluoromethylbenzaldehyde—Compound 29

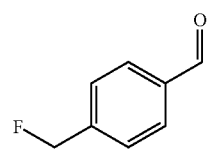

29 a) Synthesis of (4-formylphenyl)methyl methanesulfonate Compound 28

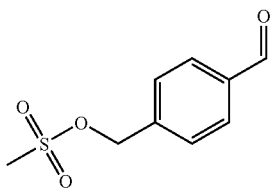

28

Mesyl chloride (12.8 µl, 0.16 mmol) was added to a solution of 4-(hydroxymethyl)benzaldehyde dimethylacetale (30 mg, 0.16 mmol) and triethyl amine (22.9 µl, 0.16 mmol) in THF. After 1 hour another equivalent of mesyl chloride and triethyl amine were added. The precipitate was filtered off after 1 hour and THF evaporated under reduced pressure. The crude product was purified using a silica short column and DCM affording 42.0 mg (98%) of pure product. (Analytical HPLC: column Phenomenex Luna 00B-4251-E0, solvents:

A=water/0.1% TFA and B=CH₃CN/0.1% TFA; gradient 5-50% B over 10 min; flow 2.0 ml/minute; retention time 4.900 minutes detected at 214 and 254 nm). Structure verified by NMR.

b) Synthesis of 4-fluoromethylbenzaldehyde—Compound 29

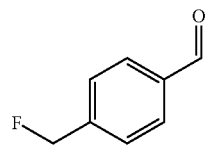

29

KF (2.7 mg, 0.047 mmol) and kryptofix 222 (17.6 mg, 0.047 mmol) were dissolved in acetonitrile (1 ml) and added to (4-formylphenyl)methyl methanesulfonate (10 mg, 0.047 mmol) in acetonitrile (1 ml). The reaction mixture was heated to 65 degrees for 10 minutes. The crude product was purified using a silica short column and diethyl ether. (Analytical HPLC: column Phenomenex Luna 00B-4251-E0, solvents: A=water/0.1% TFA and B=CH₃CN/0.1% TFA; gradient 5-50% B over 10 min; flow 2.0 ml/minute; retention time 5.1 minutes detected at 214 and 254 nm).

Example 13

Synthesis of functionalised oxytocin (disulfide Cys $^{1-6}$) analogue; [BocNHOCH₂CO-Ahx-Cys-Tyr-Ile-Gln-Asn-Cys-Pro-Leu-Gly-NH₂]-(SEQ ID NO. 1) Compound 30

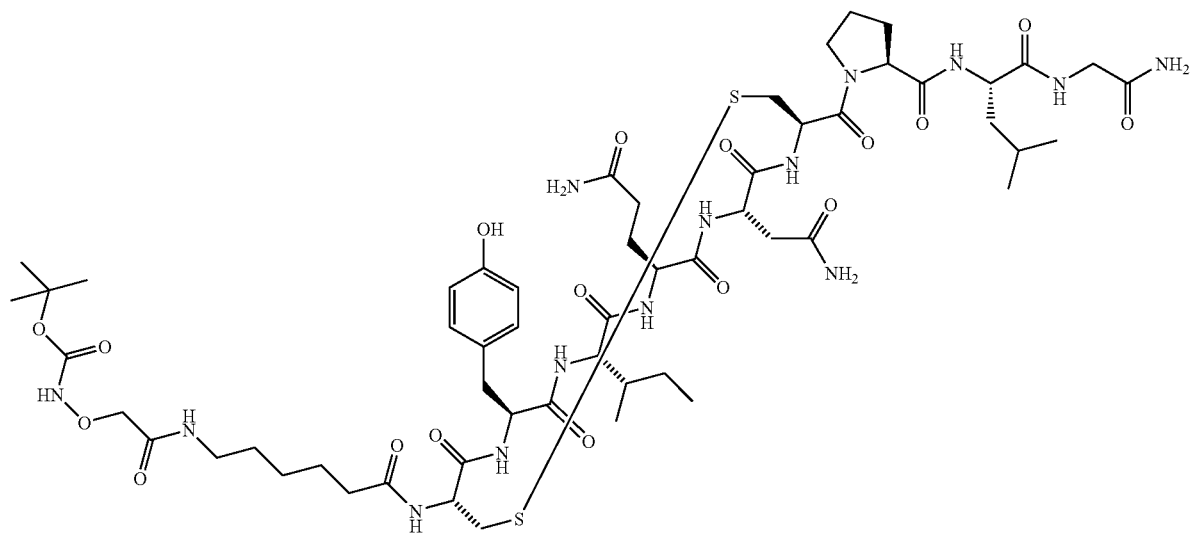

30

Protected Ahx-Cys-Tyr-Ile-Gln-Asn-Cys-Pro-Leu-Gly-NH₂ (SEQ ID NO. 1): Assembly of the amino acid sequence using fully automated synthesis (ABI 433A). The resin was placed in a manual bubbler apparatus and cleaved with TFA with 5% water and 5% TIS present. TFA was evaporated under reduced pressure after one hour. The resulting precipitate was washed with ether and air-dried. TFA and DMSO (95:5) were added to the peptide. After 2 hours TFA was evaporated under reduced pressure and diethyl ether was added to the residue. The resulting precipitate was washed with ether and air-dried. The peptide (70.6 mg, 0.063 mmol) in DMF (5 ml) was added to a solution of Boc-aminoxyacetic acid (23.9 mg, 0.13 mmol), PyAOP (65.2 mg, 0.13 mmol) and NMM (27.5 µl, 0.25 mmol) in DMF (5 ml). DMF was evaporated under reduced pressure after 12 hours. The crude product was purified by reverse phase preparative chromatography (Vydac 218TP1022 column; solvents A=water/0.1% TFA and B=CH₃CN/0.1% TFA; gradient 10-60% B over 40 min; flow 10 ml/minute; detection at 230 nm). (Analytical HPLC: Vydac 218TP54 column; solvents: A=water/0.1% TFA and B=CH₃CN/0.1% TFA; gradient 10-50% B over 20 min; flow 1.0 ml/minute; retention time 16.5 minutes detected at 214 and 254 nm). Further characterisation was carried out using mass spectrometry, giving m/z value 1293.0 [MH⁺].

Example 14

Conjugation of 4-fluoromethyl-benzaldehyde with oxytocin (disulfide Cys $^{1-6}$); [NH$_2$OCH$_2$CO-Ahx-Cys-Tyr-Ile-Gln-Asn-Cys-Pro-Leu-Gly-NH$_2$] (SEQ ID NO. 1)—Compound 31

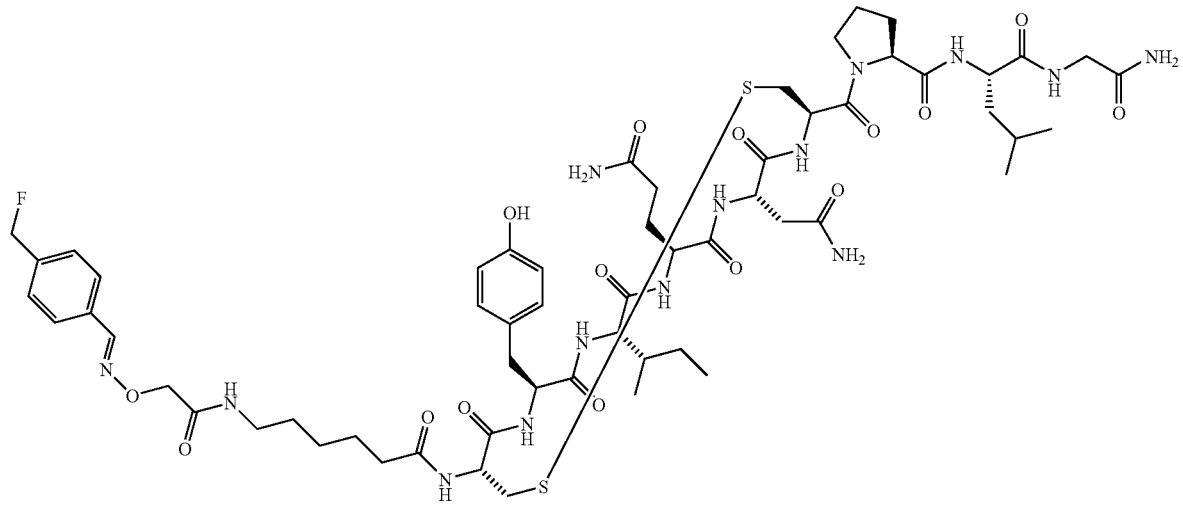

31

The Boc protecting group was cleaved from oxytocin (disulfide Cys $^{1-6}$); [Boc-NHOCH$_2$CO-Ahx-Cys-Tyr-Ile-Gln-Asn-Cys-Pro-Leu-Gly-NH$_2$] (SEQ ID NO. 1) (3.0 mg, 0.0023 mmol) using TFA and 5% water. TFA was evaporated under reduced pressure after 30 minutes and 4-fluoromethyl-benzaldehyde (1.5 mg, 0.011 mmol) dissolved in water (0.5 ml) was added and the pH adjusted with dilute ammonia to 4. The mixture was heated to 70 degrees for 50 minutes. (Analytical HPLC: column Phenomenex Luna 00B-4251-E0, solvents: A=water/0.1% TFA and B=CH$_3$CN/0.1% TFA; gradient 10-60% B over 10 min; flow 2.0 ml/minute; retention time 6.3 minutes detected at 214 and 254 nm). Further characterisation was carried out using mass spectrometry, giving m/z value 1313.1 [MH$^+$].

Example 14

Conjugation of 3-(2-fluoromethyl-phenylsulfanyl)-propionaldehyde with oxytocin (disulfide Cys $^{1-6}$); [NH$_2$OCH$_2$CO-Ahx-Cys-Tyr-Ile-Gln-Asn-Cys-Pro-Leu-Gly-NH$_2$] (SEQ ID NO. 1)—Compound 32

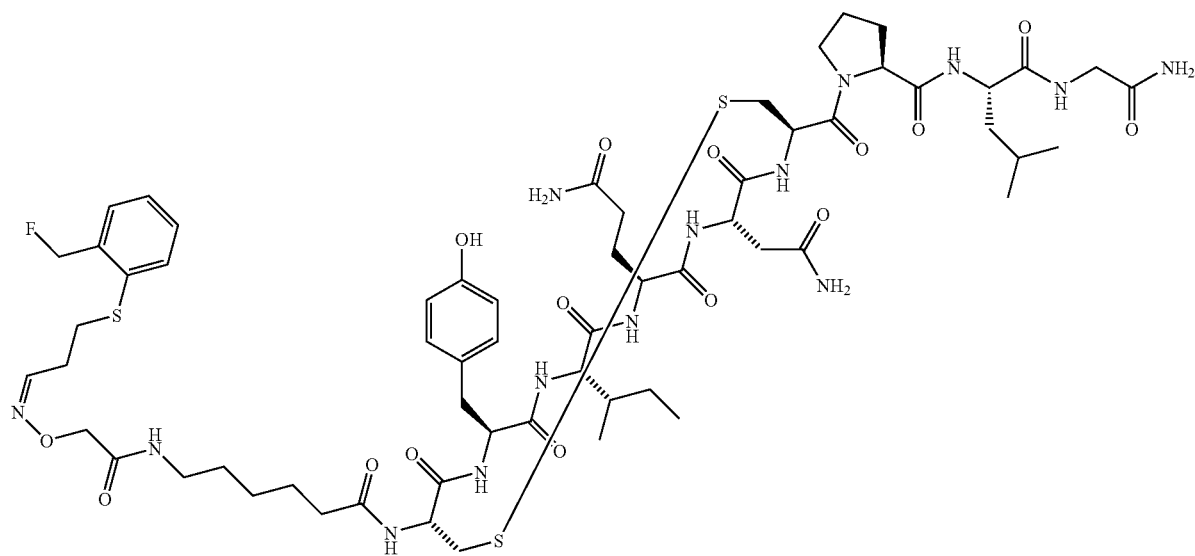

32

The Boc group was removed from the peptide moiety as described in example 6 prior to conjugation. The protecting group on 3-(2-fluoromethyl-phenylsulfanyl)-propionaldehyde (0.81 mg, 0.0034 mmol) was removed using 1N HCl in acetonitrile (1:1) 0.1 ml. The mixture was left for 30 minutes before it was added to the peptide (2.0 mg, 0.0017 mmol) in 0.4 ml water and pH adjusted to 4 with dilute ammonia. The mixture was heated to 70 degrees for 50 minutes. (Analytical HPLC: Vydac 218TP54 column, solvents: A=water/0.1% TFA and B=CH$_3$CN/0.1% TFA; gradient 10-50% B over 20 min; flow 1.0 ml/minute; retention time 19.8 minutes detected at 214 and 254 nm). Further characterisation was carried out using mass spectrometry, giving m/z value 1373.5 [MH$^+$].

Example 15

Conjugation of Compound 7 with oxytocin (disulfide Cys $^{1-6}$); [NH$_2$OCH$_2$CO-Ahx-Cys-Tyr-Ile-Gln-Asn-Cys-Pro-Leu-Gly-NH$_2$] (SEQ ID NO. 1)—Compound 33

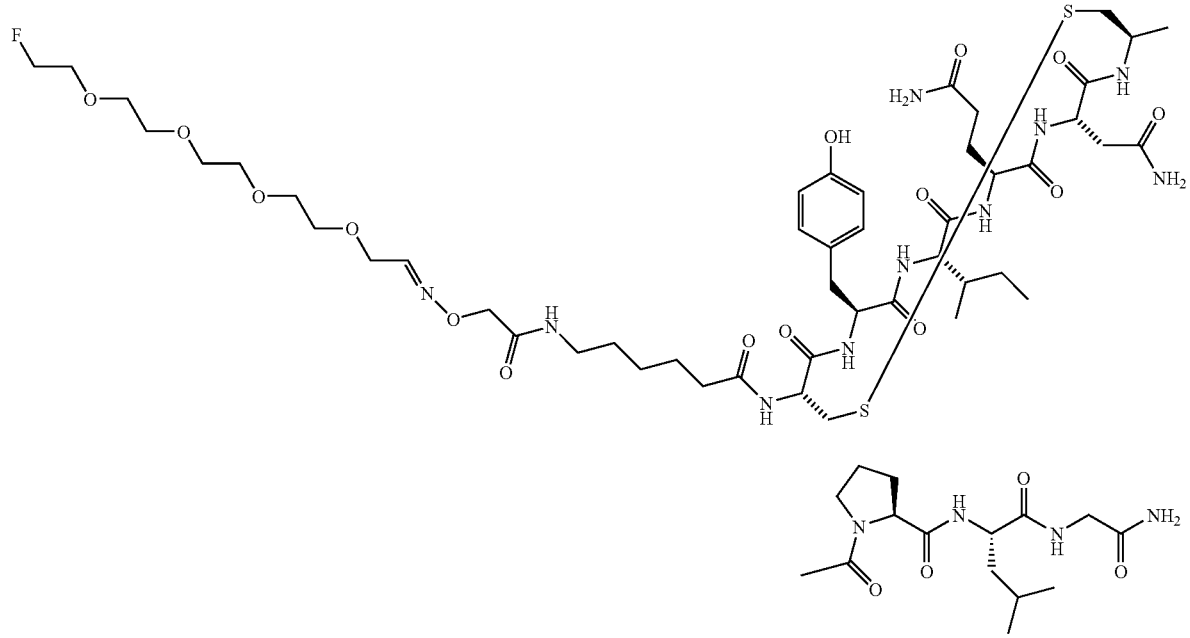

33

40

The Boc protecting group was cleaved from oxytocin (disulfide Cys $^{1-6}$); [Boc-NHOCH$_2$CO-Ahx-Cys-Tyr-Ile-Gln-Asn-Cys-Pro-Leu-Gly-NH$_2$] (SEQ ID NO. 1) (2.5 mg, 0.0019 mmol) using TFA and 5% water. TFA was evaporated under reduced pressure after 30 min. The protecting group on compound 7 (1.0 mg, 0.0041 mmol) was removed using 1N HCl in acetonitrile (1:1) 0.5 ml. The mixture was left for 30 minutes before it was added to the peptide and pH adjusted to 4 with dilute ammonia. The mixture was heated to 70 degrees for 15 minutes. (Analytical HPLC: column Vydac 218TP54 column, solvents: A=water/0.1% TFA and B=CH$_3$CN/0.1% TFA; gradient 10-50% B over 20 min; flow 1.0 ml/minute; retention times 15.1 and 15.4 minutes detected at 214 and 254 nm). Further characterisation was carried out using mass spectrometry, giving m/z value 1413.5 [MH$^+$].

The invention described and claimed herein is not to be limited in scope by the specific embodiments herein disclosed, since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for radiofluorination comprising reaction of a compound of formula (I) with a compound of formula (II):

R1—[vector]   (I)

$^{18}$F-(Linker)-R2   (II)

or, a compound of formula (III) with a compound of formula (IV)

R3—[vector]   (III)

$^{18}$F-(Linker)-R4   (IV)

wherein
R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
R2 is a group selected from primary amine, secondary amine, hydroxylamine, hydrazine, hydrazide, aminoxy, phenylhydrazine, semicarbazide, and thiosemicarbazide and is preferably a hydrazine, hydrazide or aminoxy group;
R3 is a group selected from primary amine, secondary amine, hydroxylamine, hydrazine, hydrazide, aminoxy, phenylhydrazine, semicarbazide, or thiosemicarbazide, and is preferably a hydrazine, hydrazide or aminoxy group;
R4 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
to give a conjugate of formula (V) or (VI) respectively:

$^{18}$F-(Linker)-X—N=⟨Y⟩—[vector]   (V)

-continued

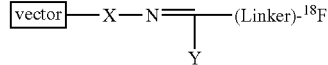

(VI)

wherein X is —CO—NH—, —NH—, —O—, —NH-CONH—, or —NHCSNH—, and is preferably —CO—NH—, —NH— or —O—; Y is H, alkyl or aryl substituents; and
the Linker group in the compounds of formulae (II), (IV), (V) and (VI) is selected from

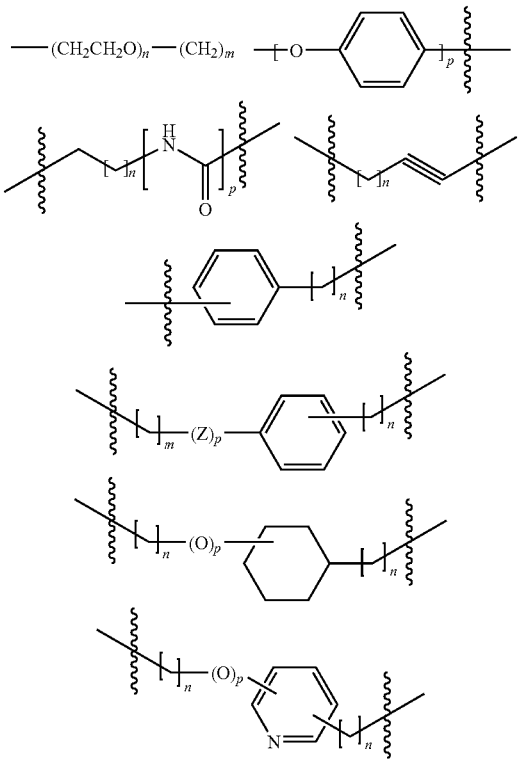

wherein:
n is an integer of 0 to 20;
m is an integer of 1 to 10;
p is an integer of 0 or 1;
Z is O or S.

2. A method according to claim 1 wherein the vector is Arg-Gly-Asp peptide or an analogue thereof.

3. A method according to claim 2 wherein the vector comprises the fragment

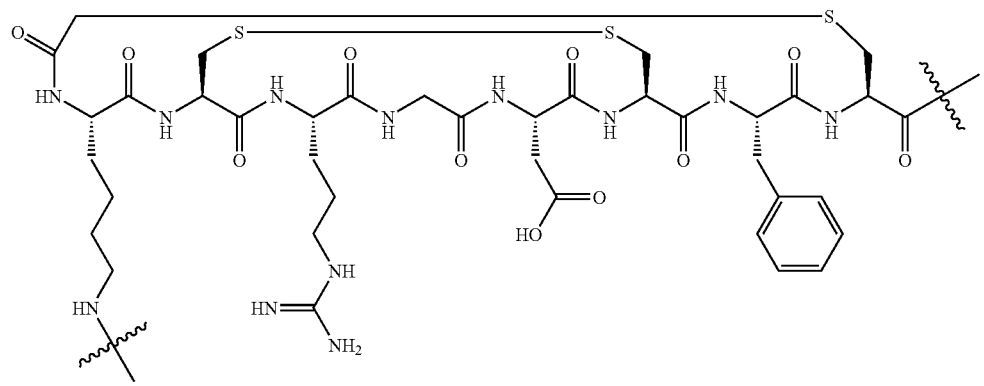

4. A method according to claim 2 wherein the vector is of formula (A):

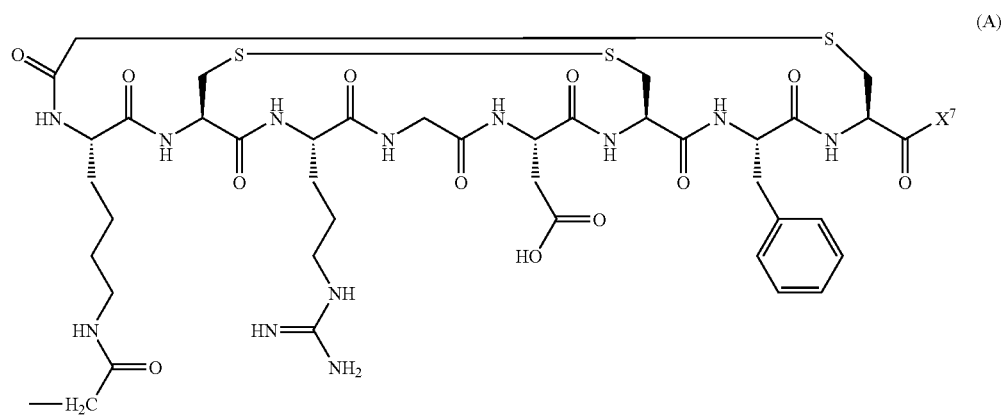

wherein $X^7$ is either —NH$_2$ or

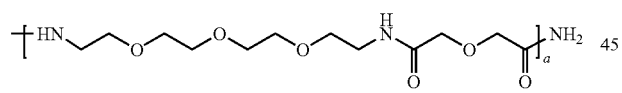

wherein a is an integer of from 1 to 10, preferably a is 1.

5. A compound of formulae (V) or (VI) prepared according to method of claim 1.

6. A compound according to claim 5 wherein the vector is Arg-Gly-Asp peptide or an analogue thereof.

7. A compound according to claim 6 wherein the vector comprises the fragment:

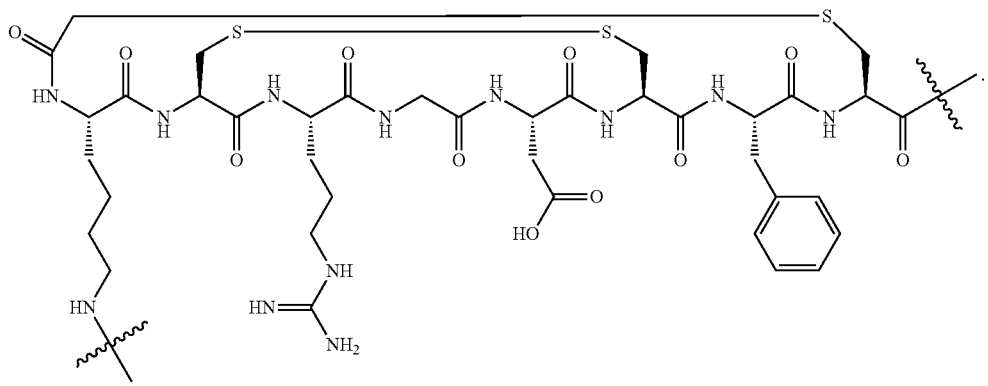

8. A compound according to claim 6 wherein the vector is of formula (A):

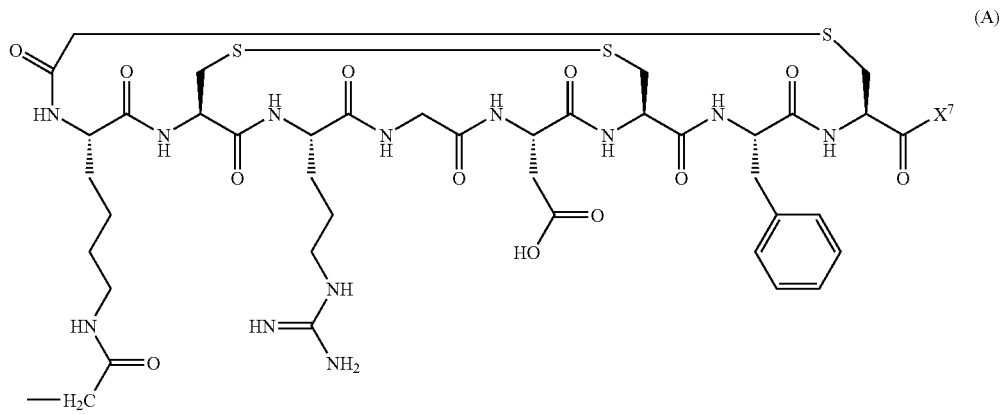

(A)

wherein $X^7$ is either —NH$_2$ or

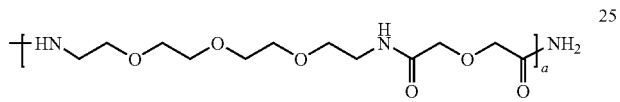

wherein a is an integer of from 1 to 10, preferably a is 1.

9. A radiopharmaceutical composition comprising an effective amount of a compound according to claim 5; together with one or more pharmaceutically acceptable adjuvants, excipients or diluents.

10. A method for radiofluorination comprising reaction of a compound of formula (Ia) with a compound of formula (IIa):

(Ia)

(IIa)

or, a compound of formula (IIIa) with a compound of formula (IVa)

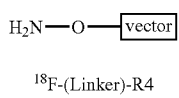

(IIIa)

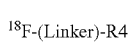

(IVa)

wherein R1 and R4 are as defined in claim 1;

the Linker group in the compounds of formulae (IIa) and (IVa) are each a $C_{1-60}$ hydrocarbyl group, suitably a $C_{1-30}$ hydrocarbyl group, optionally including 1 to 30 heteroatoms, suitably 1 to 10 heteroatoms such as oxygen or nitrogen;

to give a conjugate of formula (Va) or (VIa) respectively:

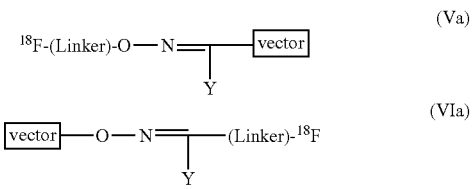

(Va)

(VIa)

wherein Y is H, alkyl or aryl substituents; and the Linker group is as defined for the compound of formula (IIa) or (IVa).

11. A compound of formula (Va) or (VIa) prepared according to method of claim 10.

12. A method for radiofluorination comprising reaction of a compound of formula (VII):

(VII)

with a compound of formula (VIII), (IX), (X) or (XI):

(VIII)

(IX)

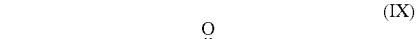

(X)

(XI)

wherein:

n is an integer of 0 to 20;

m is an integer of 1 to 10;

X is —CO—NH—, —NH— or —O— and is preferably —O—

Y is H, alkyl or aryl substituents to give a compounds of formula (XII-XV) respectively:

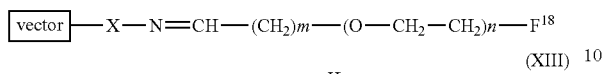
(XII)

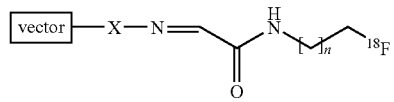
(XIII)

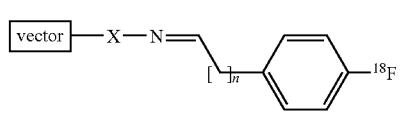
(XIV)

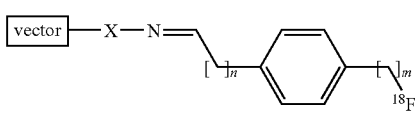
(XV)

wherein X is as defined for the compound of formula (VII), m and n are defined as for the compounds of formula (VIII to XI).

13. A compound of formula (XII), (XIII), (XIV), (XV) prepared according to method of claim 12.

14. A method for radiofluorination comprising reaction of a compound of formula (XVI):

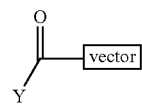
(XVI)

where Y is H, alkyl or an aryl substituent preferably with compounds of the formula (XVII), (XVIII),(XIX) or(XX):

(XVII)
$^{18}F—(CH_2—CH_2—0)_n—(CH_2)_m—W—NH_2$

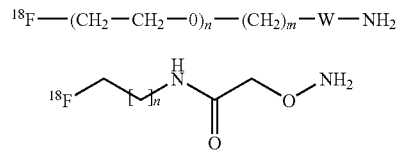
(XVIII)

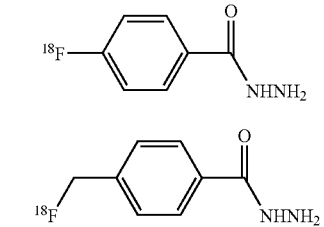
(XIX)

(XX)

wherein m is an integer of 1 to 10, n is an integer of 0 to 20, and W=—CONH—, —NH— or —O— to give a compound of formula (XXI), (XXII), (XXIII) or (XXIV) respectively:

(XXI)
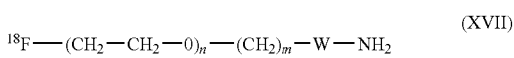

(XXII)
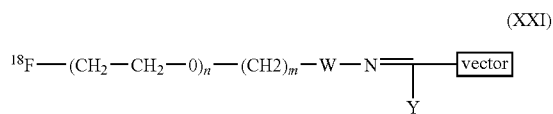

(XXIII)
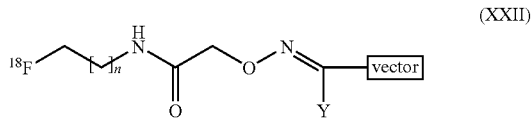

(XXIV)

wherein W=—CONH—, —NH— or —O—, m, n, are as defined for the compounds of formula (XIII to XI) and Y is H, alkyl or aryl moiety.

15. A compound of formula (XXI), (XXII), (XXIII), (XXIV) prepared according to method of claim 14.

16. A compound of formula (II) $^{18}$F-(Linker)-R2 or a compound of formula (IIa) $^{18}$F-(Linker)-O—NH$_2$, with the proviso that:

in the compounds of formula (II), if the linker is phenyl then R2 is aminoxy (suitably —ONH$_2$).

17. A compound of formula (XVII), (XVIII), (XIX), or (XX):

(XVII)
$^{18}F—(CH_2—CH_2—0)_n—(CH_2)_m—W—NH_2$

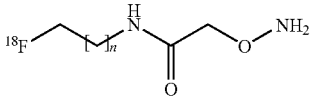
(XVIII)

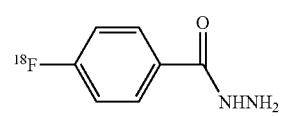
(XIX)

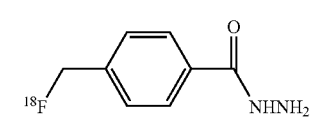
(XX)

wherein m is an integer of 1 to 10, n is an integer of 1 to 20, and W =—CONH—, —NH— or —O—.

18. A compound of formula (IV) $^{18}$F-(Linker)-R4 or a compound of formula (IVa) $^{18}$F-(Linker)-R4; with the provisos that:
(i) in the compounds of formula (IV), the linker is not phenyl
(ii) in the compounds of formula (IVa), the linker is not phenyl or phenyl substituted by halo, hydroxy, or benzyloxy.

19. A compound of formula (VIII), (IX), (X), or (XI):

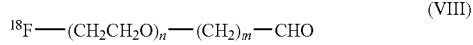
(VIII)

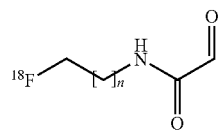
(IX)

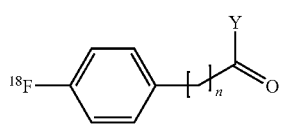
(X)

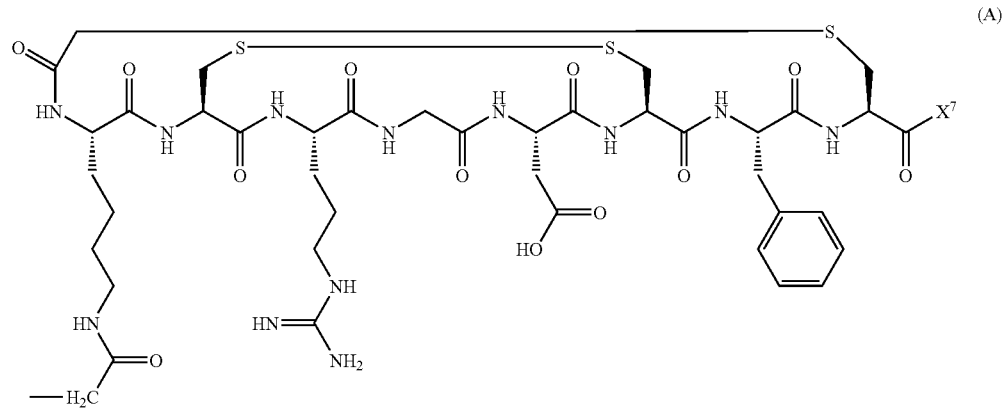
(XI)

wherein:
n is an integer of 1 to 20;
m is an integer of 1 to 10;
Y is H, alkyl or aryl substituents
with the proviso that in the compounds of formula (X), n is 1 to 20.

20. A compound of formula

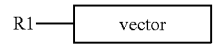

(I) or a compound of formula

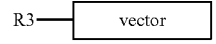

(III) wherein R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent; and R3 is a group selected from primary amine, secondary amine, hydroxylamine, hydrazine, hydrazide, aminoxy, phenylhydrazine, semicarbazide, or thiosemicarbazide, and is preferably a hydrazine, hydrazide or aminoxy group.

21. A compound according to claim 20 wherein the vector is Arg-Gly-Asp peptide or an analogue thereof.

22. A compound according to claim 20 wherein the vector is of formula (A):

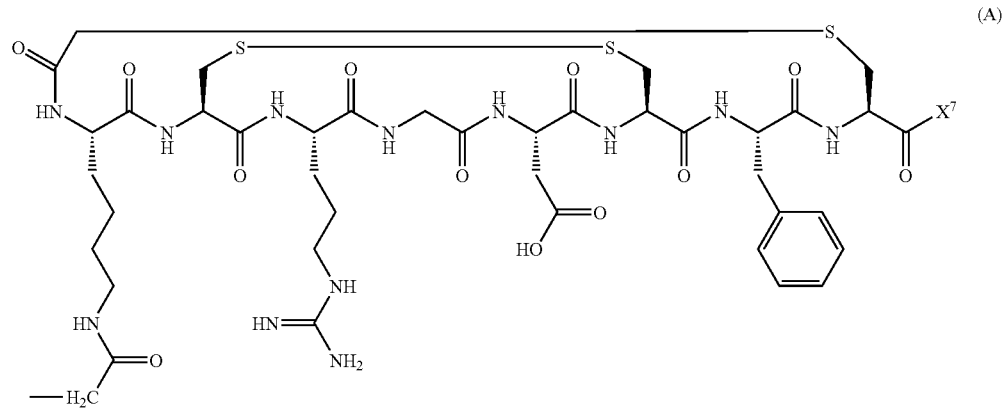
(A)

wherein $X^7$ is either —NH$_2$ or

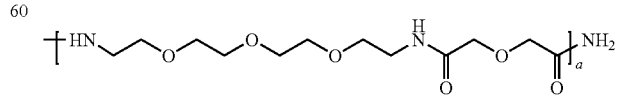

wherein a is an integer of from 1 to 10, preferably a is 1.

23. The compound of formula:

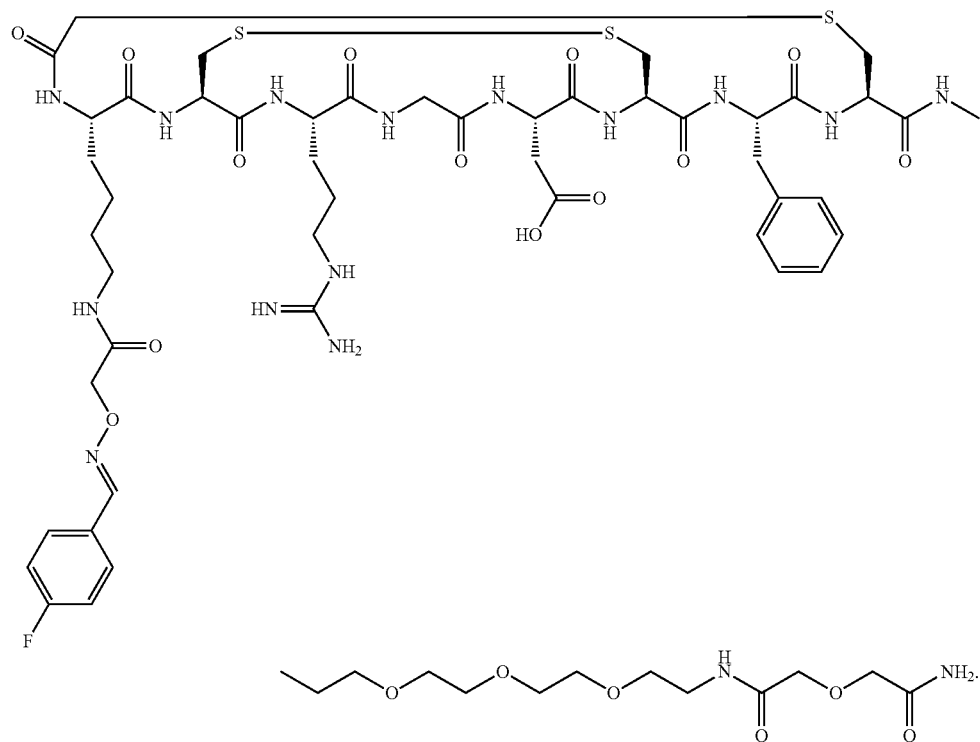

24. A compound of formula

R1—[vector]

(Ia) or a compound of formula

R3—[vector]

(IIIa) wherein R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent; and R3 is a group selected from primary amine, secondary amine, hydroxylamine, hydrazine, hydrazide, aminoxy, phenylhydrazine, semicarbazide, or thiosemicarbazide, and is preferably a hydrazine, hydrazide or aminoxy group.

25. A compound according to claim 24 wherein the vector is Arg-Gly-Asp peptide or an analogue thereof.

26. A compound according to claim 24 wherein the vector is of formula (A):

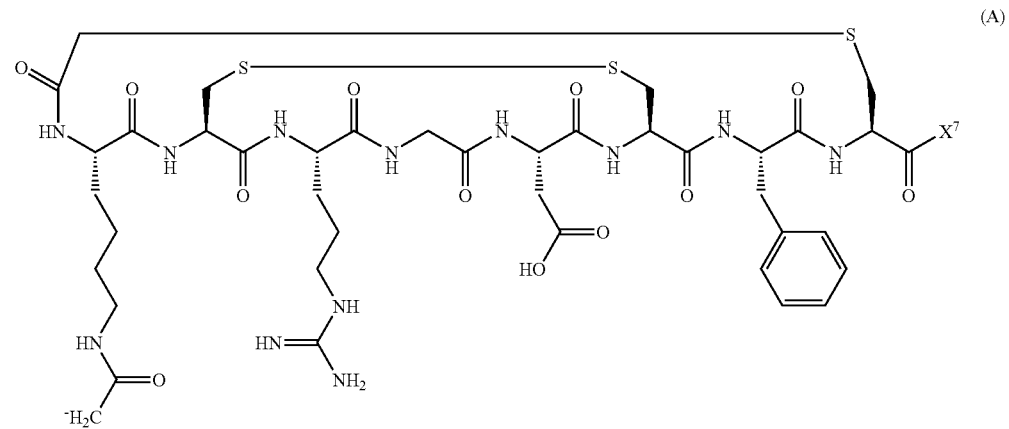

wherein $X^7$ is either —$NH_2$ or
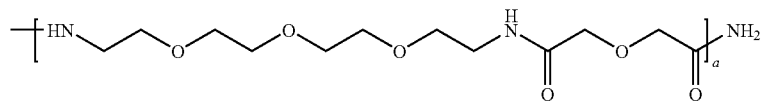
wherein a is an integer of from 1 to 10, preferably a is 1.
* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Cys Tyr Ile Gln Asn Cys Pro Leu Gly
1               5